(12) United States Patent
Brakhya et al.

(10) Patent No.: US 12,256,909 B2
(45) Date of Patent: Mar. 25, 2025

(54) ENDOSURGICAL DEVICE

(71) Applicant: Multi4 Medical AB, Jönköping (SE)

(72) Inventors: Ronny Brakhya, Huskvarna (SE);
Hannes Ulvegard, Jönköping (SE);
Robert Axelsson, Gränna (SE); Miden Melle Hannah, Jönköping (SE); Noomi Altgärde, Huskvarna (SE)

(73) Assignee: Multi4 Medical AB, Jönköping (SE)

( * ) Notice: Subject to any disclaimer, the term of this patent is extended or adjusted under 35 U.S.C. 154(b) by 866 days.

(21) Appl. No.: 17/312,873

(22) PCT Filed: Dec. 3, 2019

(86) PCT No.: PCT/EP2019/083436
§ 371 (c)(1),
(2) Date: Jun. 10, 2021

(87) PCT Pub. No.: WO2020/120219
PCT Pub. Date: Jun. 18, 2020

(65) Prior Publication Data
US 2022/0054114 A1 Feb. 24, 2022

(30) Foreign Application Priority Data
Dec. 14, 2018 (SE) .................................. 1851591-6

(51) Int. Cl.
*A61B 10/04* (2006.01)
*A61B 1/00* (2006.01)
(Continued)

(52) U.S. Cl.
CPC .......... *A61B 10/04* (2013.01); *A61B 1/00016* (2013.01); *A61B 1/00068* (2013.01);
(Continued)

(58) Field of Classification Search
None
See application file for complete search history.

(56) References Cited

U.S. PATENT DOCUMENTS

2018/0125567 A1   5/2018   Ciccone et al.

FOREIGN PATENT DOCUMENTS

| EP | 1665993 A1 | 6/2006 |
|----|------------|--------|
| EP | 3329858 A1 | 6/2018 |

(Continued)

OTHER PUBLICATIONS

International Search Report for International Application No. PCT/EP2019/083436, mailed Mar. 3, 2020 (3 pages).

*Primary Examiner* — Aurelie H Tu
(74) *Attorney, Agent, or Firm* — Kagan Binder, PLLC

(57) ABSTRACT

A multi-functional endosurgical device (1) comprises a tube (3), an end effector (21), and a device operating part (4). The tube (3) several lengthwise extending channels (9) for supplying a liquid and suction to the end effector (21) and to apply current to perform diathermy. A slide rail assembly (5) comprises at a main slide guide body (46) that accommodates an end effector slider (47) and a junction slider (48). The end effector slider (47) slides in the guideway (54) and is connected to the effector sleeve (17) through one of the lengthwise extending channels to operate said effector sleeve (17) in relation to the end effector. The junction slider (48) also slides in the guideway (54) downstream the end effector slider (47). The junction slider (48) is connected to the tube (3) to arrange at least a first lengthwise extending channel (9), a second lengthwise extending channel (10) and a third lengthwise extending channel (15) of the tube (3) in communication with the end effector (21).

19 Claims, 12 Drawing Sheets

Figure 4:
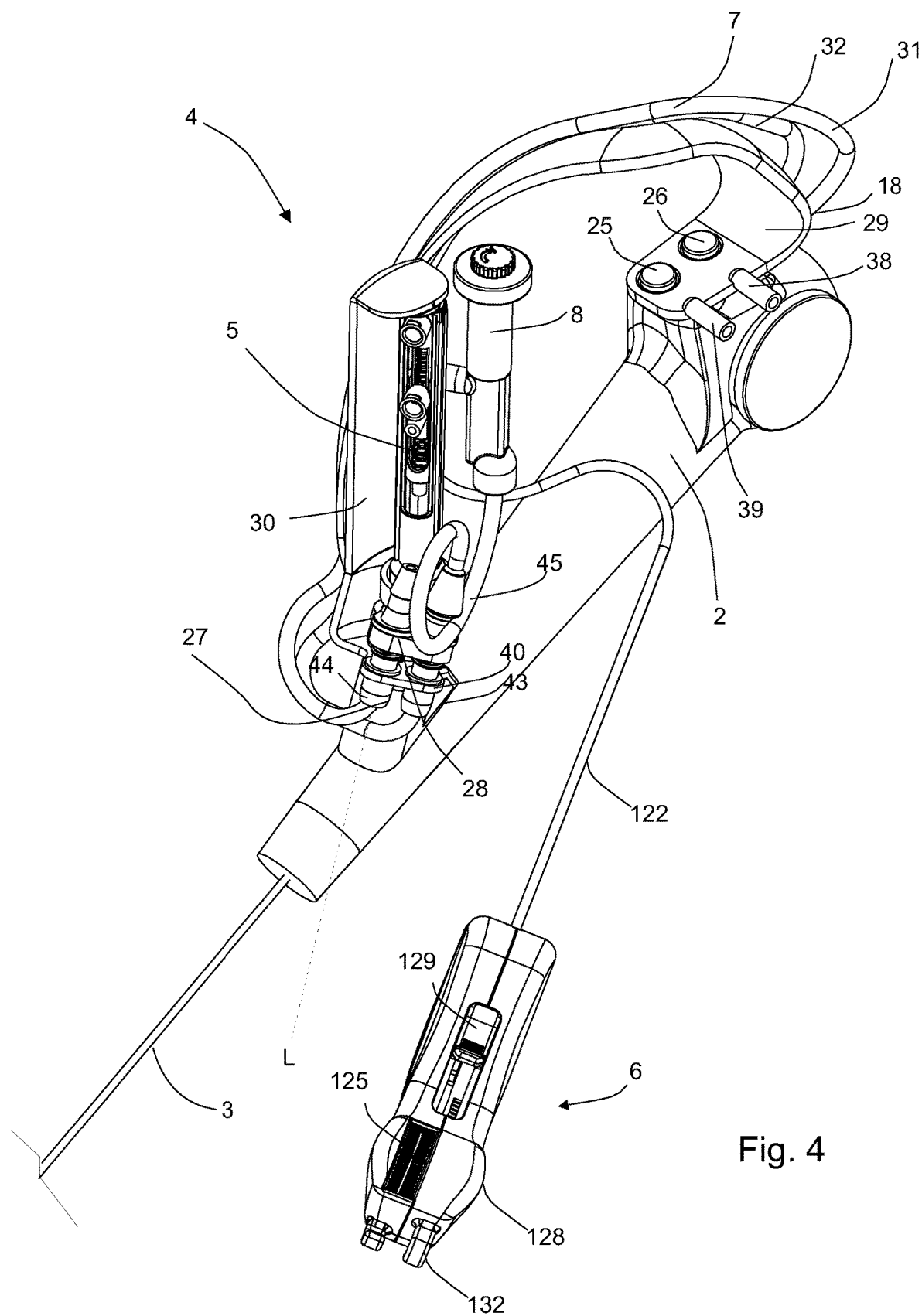

(51) Int. Cl.
*A61B 1/015* (2006.01)
*A61B 1/307* (2006.01)
*A61B 10/06* (2006.01)

(52) U.S. Cl.
CPC ...... *A61B 1/00091* (2013.01); *A61B 1/00121* (2013.01); *A61B 1/015* (2013.01); *A61B 1/307* (2013.01); *A61B 10/06* (2013.01); *A61B 2217/005* (2013.01); *A61B 2217/007* (2013.01)

(56) References Cited

FOREIGN PATENT DOCUMENTS

| WO | 9833436 A1 | 8/1998 |
| WO | 2006078743 A1 | 7/2006 |
| WO | 2016161011 A1 | 10/2016 |
| WO | 2016188540 A1 | 12/2016 |

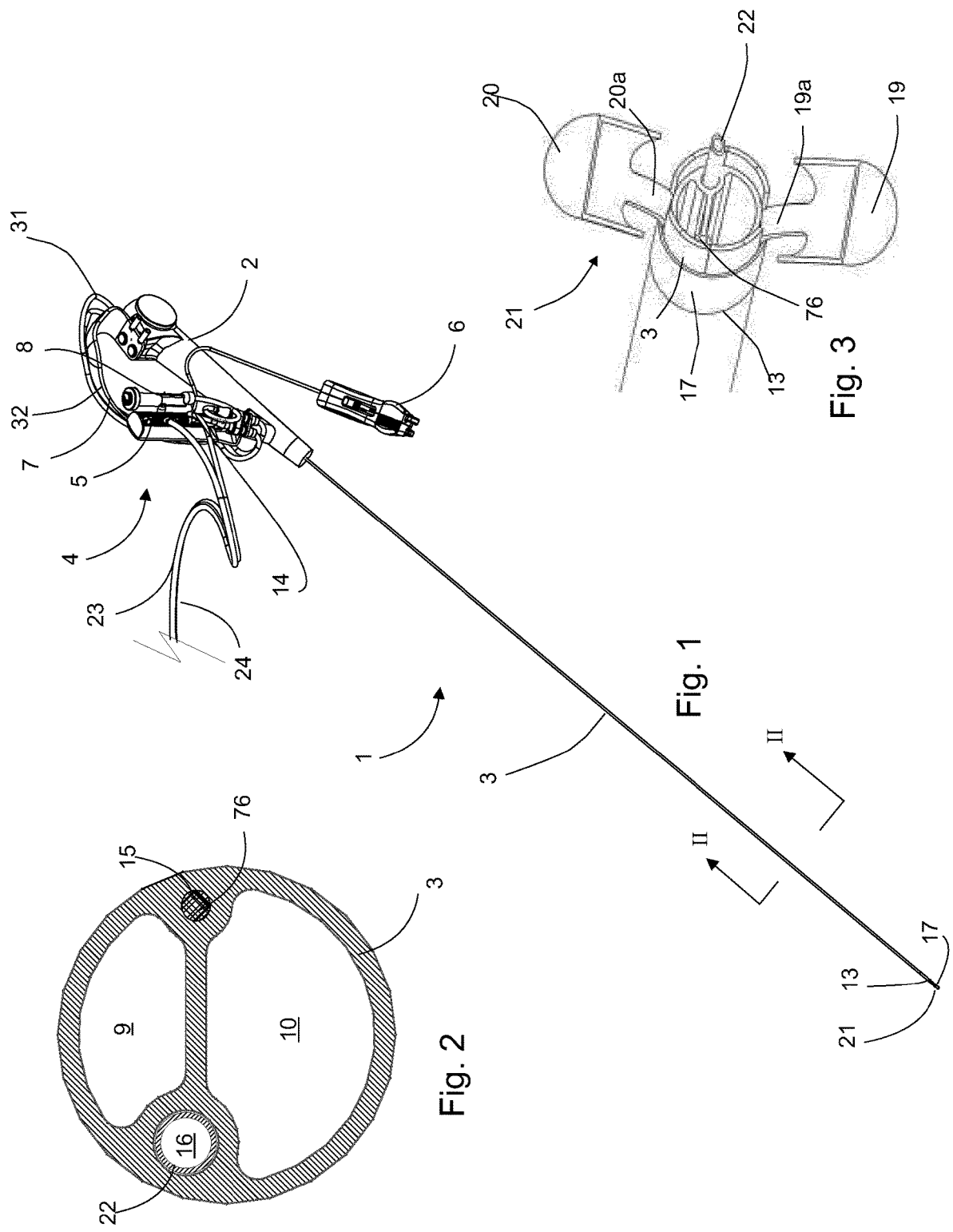

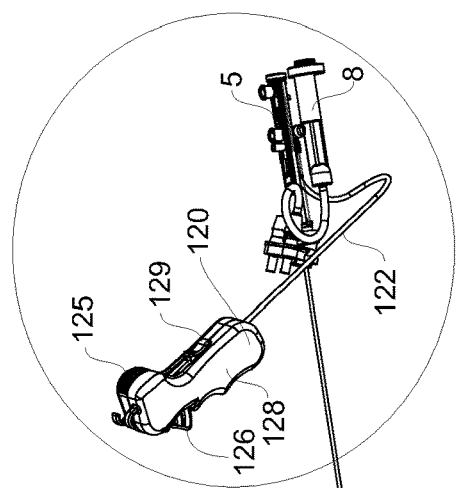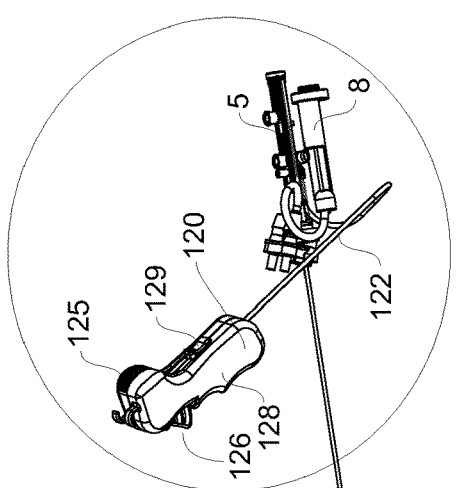
Fig. 15
Fig. 16

ENDOSURGICAL DEVICE

CROSS-REFERENCE TO RELATED APPLICATIONS

This application claims priority to International Application No. PCT/EP2019/083436, filed Dec. 3, 2019 and titled "AN ENDOSURGICAL DEVICE," which in turn claims priority from a Swedish Patent Application having serial number 1851591-6, filed Dec. 14, 2018, titled "AN ENDOSURGICAL DEVICE," both of which are incorporated herein by reference in their entireties.

The present invention relates to an endosurgical device, comprising:
- a tube having a proximal tube end and an opposite distal tube end, and at least one lengthwise extending channel extending there between,
- an end effector provided at the distal tube end, and a device operating part at the proximal tube end.

Urinary bladder cancer is one of the most expensive forms of cancer in Sweden and internationally. In the United States estimated costs are about 140,000 dollars per newly diagnosed person. Every year there are about 2,400 new persons in Sweden diagnosed with urinary bladder cancer. In the past 20 years, the number of cases has increased by a total of 35 percent and urinary cancer affects men three times as often as women. Cancer in the urinary bladder and urinary tract is the third most common form of cancer in men in Sweden.

About 70% of patients have a superficial urinary bladder cancer form restricted to the mucosa. This means that these patients can be cured, but unfortunately there is a risk of recurrence and of residual tumor. About two thirds of patients need a new surgery. It is not uncommon for one and the same patient to undergo several operations, sometimes only a few months after the first. There will be many regular visits to the urologist to discover recurrence early so that the cancer does not grow.

Cystoscopy is the primary diagnostic modality for the diagnosis of bladder carcinoma. A conventional cystoscope normally has two ports, an optical port that permits to see inside the bladder and an instrument port for insertion of various devices. The endosurgical device of the present invention is of the kind to be inserted via the instrument port of an endoscope, and may advantageously be an endosurgical biopsy device.

If a cancer or a suspicious area is seen during the cystoscopy the patient is normally planned for a surgery at an operation theatre and then stays one night at the urology ward. In Sweden the patient needs to wait for about two weeks for this surgery and normally the patient receives a spinal anesthesia or general anesthesia before the procedure can be performed at a surgery department. During the biopsy procedure tissue specimens are taken with rigid metal instruments or a transurethral resection is performed also with rigid metal instruments. At some hospitals, biopsies can be performed as an outpatient procedure with flexible cystoscope but since the quality of the tissue specimens are not good enough with flexible biopsy instruments, rigid instruments that have a larger diameter need to be used to receive better tissue specimens and to be able to resect the cancer.

During cystoscopy, when there is suspicion of cancer in the urinary bladder, the urologist generally obtains multiple bladder tissue specimens, typically using a punch biopsy forceps, from various locations in the bladder to help establish the diagnosis and to determine the extent of a potential tumor. Generally tissue specimens are taken from any areas of abnormal-looking urothelium and from suspected tumor areas, but typically from trigone, bladder dome, and right, left, anterior and posterior bladder walls. At the time of the procedure, the bladder is lavaged with fluid. Prior to tissue acquisition during a transurethral bladder biopsy using a flexible cystoscope local anesthesia can be made at the sample site or anesthesia is obtained locally by instilling anesthetic agents into the bladder. Following tissue acquisition, the biopsy site is cauterized for hemostasis, and the procedure is repeated. Because a conventional cystoscope only has one working channel for the various devices needed during the surgical procedure, each of these various devices is moved in and out of the working channel each time a tissue specimen is taken from the bladder. In the past it has not been possible to only use one instrument to give anesthesia, take one or multiple biopsies, stop bleedings, and destruct small cancers in the bladder. Also because of the small dimensions the quality of the biopsy is not good enough because the important layers in the bladder wall needed to be seen in the microscope is not included. Since biopsies are taken today by pulling out the instruments when the jaws get caught in the tissue, the edges of the tissue sample are destroyed, and the quality of the tissue samples is decreased and can't be used to diagnose the cancer accurate.

The article "A system of multiple biopsy forceps", by Thomas V. Taylor, Curr. Surg. 2004 November-December; 61(6): pages 594-596 describes a new system of flexible endoscopic biopsy forceps, that should take larger and less traumatized biopsies than existing single biopsy forceps. The device utilizes a central wire with a barbed spike at one end, to which sliding sprung steel jaws are attached. An outer plastic sleeve surrounds the central wire, and conventional-type handles activate the jaws. This known device is passed along the working channel of a fiber optic endoscope, and the tissue to undergo biopsy is visualized. Opening and closing of the forceps occurs when the outer sleeve slides on the inner wire allowing the sprung steel jaws to open and close. With the jaws open, the barb is pushed into the tissue to undergo biopsy. The fishhook-like barb pulls back the tissue into the jaws, which bite the tissue at an angle and can thus obtain cleaner and bigger tissue specimens. For the second biopsy, the jaws are simply reopened, and as the barbed spike again pierces the tissue, the first specimen is pushed along the central wire. Up to 6 biopsies are to be stored in this way with a single passage of the biopsy forceps through the endoscope. All tissue specimens are retracted all together with the device when said device is retracted from the fiber optic endoscope. However the fishhook-like barb injures the tissue specimen, which must be teased off the fishhook-like barb with another pair of forceps, or the tip of the barb is pushed into a piece of cork and the specimens cut off. Both ways downsize each tissue specimen, thereby affecting specimen integrity and casting doubt on precise origin and orientation of surfaces in relation to organ biopsy site. So because the tissue specimen needs to be manipulated off the barb the origin and orientation of the specimens can be difficult to keep under control. Furthermore the barb-type kind of biopsy device is rather brutal to both patient and the tissue specimens, has no means for local anesthesia, no means for stopping local bleeding at the sampling site, and since 6 tissue specimens are stored along the barb simultaneously the front end must be rather large.

The article "Flexible cystoscopic bladder biopsies: a technique for outpatient evaluation of the lower urinary tract urothelium" by Marc Beaghler and Michael Grasso in Urology. 1994 November; 44(5):756-9, describes a monopolar technique to obtain biopsies requiring an active electrical cord that adapts to the biopsy forceps and a standard electrocautery device. A grounding pad is placed on the patient's thigh. To obtain a biopsy, the forceps is advanced through the working channel of the cystoscope. The target area is engaged by toothed jaws of a forceps under direct vision and coagulation current is applied while withdrawing to cause blanching of the surrounding urothelium. The cystoscope and the tissue specimen are removed as one unit, and the cystoscope must be reinserted to inspect biopsy site, bleeding and to take further tissue specimens.

It is thus known that tissue specimens can be resected or excised using various kinds of effector tools, the most common being a forceps. Monopolar electrocautery systems have been introduced in cystoscopy in attempts to reduce the risk of complications and produce better tissue specimens for the pathologists, however until now these monopolar electrocautery systems tend to apply too much heat to the tissue specimen, which destroys the cancer cells and makes the tissue specimen unusable for cancer diagnostics.

The applicant has realized that operation of an endoscope with inserted endosurgical instrument involves assistance by several persons besides the primary operator, and that collecting and subsequent handling of tissue specimens are done very different from patient to patient, amongst surgeons and at different institutions.

The applicant's Swedish patent application no. 1751639-4 filed 22 Dec. 2017 concerns an improved endosurgical device by means of which tissue specimens can be taken in a gentle biopsy procedure, e.g. on an office as an outpatient procedure instead, often without general anesthesia.

Most resected tissue specimens are about 1.5 mm in diameter and 20 mm in length, whereas excisional specimens range from 1 cm in diameter to larger. The dimensions of the closed end effector and of the lengthwise extending channels of the endosurgical instrument of the present invention, and of the device described in Swedish patent application no. 1751639-4, set the limit for size and length of the tissue specimens obtainable by said endosurgical instruments.

The manner in which the tissue specimens are taken, temporarily accommodated, and subsequently prepared has a dramatic impact on the pathology and of the histological results. The failure to appreciate and standardize thickness of tissue specimen, orientation of the tissue specimen, time until fixation, and the fixation process itself poses, are all parameters involved for the analyst to make the best possible histomorphologic diagnosis on the tissue specimen.

In case the suspect organ is the bladder the biopsy procedure recommends a total of seven biopsies to be performed of masses and/or tissue. The tissue specimens are transferred one after another to individual vials properly labeled prior to the biopsy procedure. Information on the label includes identification data of the patient and optionally the origin and the exact biopsy site of the relevant tissue specimen, or other identification that links the vial to the specific origin of tissue specimen.

It has been realized that there is a need within the art for an improved endosurgical device that the operator can work alone, or with minimum additional assistance, when acquiring tissue specimens from a hollow organ, such as a body cavity, or other tissue surface via an access channel of an endoscope, such as a flexible endoscope. The flexible endoscope may be a cystoscope and the organ the urinary bladder.

In a main aspect of the present invention is provided an endosurgical device of the kind mentioned in the opening paragraph, which device has multiple functions that can be activated while the device is still inserted in the endoscope's working channel, so that the device need not to be moved in and out of said working channel many times for completing the required numbers of biopsies in a non-destructive and safe manner.

In yet an aspect of the present invention is provided an endosurgical device of the kind mentioned in the opening paragraph, which device can be operated for taking multiple biopsies through an endoscope inserted in a body cavity and without having to reinsert the endoscope in the body cavity each time a tissue specimen has been taken.

In yet an aspect of the present invention is provided an endosurgical device of the kind mentioned in the opening paragraph in form of an endoscopic biopsy forceps that are simple, cheap to produce, and disposable.

In yet an aspect of the present invention is provided an endosurgical device of the kind mentioned in the opening paragraph with an improved operative functionality.

In yet an aspect of the present invention is provided an endosurgical device of the kind mentioned in the opening paragraph that can be operated by a lower number of persons than for conventional devices for same purposes.

In yet an aspect of the present invention is provided a biopsy sample collecting device and sample collecting system for an endosurgical device of the kind mentioned in the opening paragraph.

In yet an aspect of the present invention is provided a multi-functional endosurgical device for taking several tissue specimens, in particular for taking tissue specimens from the urinary bladder.

The novel and unique whereby these and other aspects are achieved according to the present invention consists in that the endosurgical device comprises that the tube has at least a first lengthwise extending channel for supplying a liquid to the end effector, a second lengthwise extending channel for removing matter from or at the end effector, and a third lengthwise extending channel for accommodating an electrical wire connected to the end effector to apply current to perform diathermy, an effector sleeve surrounding the tube at least at the distal tube end of said tube, and being arranged to reciprocate at least at the distal tube end of the tube, the device operating part comprising a slide rail assembly, which slide rail assembly comprises at least a main slide guide body that accommodates at least an end effector slider and a junction slider, the main slide guide body has a guideway with a proximal guide end and an opposite distal guide end that receives the tube, the end effector slider is adapted to reciprocatingly slide in the guideway at the distal guide end to operate said effector sleeve in relation to the end effector, and the junction slider is adapted to reciprocatingly slide in the guideway between the proximal guide end and the end effector slider, which junction slider is connected to the tube to arrange at least the first lengthwise extending channel, the second lengthwise extending channel and the third lengthwise extending channel of the tube in communication with the end effector.

By using the term "diathermy" in the context of the present invention is meant that the end effector, e.g. the jaws, of the endosurgical device are adapted to generate heat in organ tissue by high-frequency electromagnetic currents. The high-frequency electromagnetic currents pass through tissue and make a precise surgical incision like a scalpel blade, whereby the surgical diathermy provides fine, precise incisions and tissue specimens.

The end effector slider is adapted to slide in the guideway to operate the effector sleeve in relation to the end effector by being connected to the effector sleeve via a reciprocatable connecting means surrounding the tube, such as a coil member on the outside of the tube, or a reciprocatable connecting means inside the tube, e.g. an effector wire inside one of the lengthwise extending channels.

The tube has the effector sleeve at its distal tube end, which effector sleeve is adapted to reciprocate along the length of the tube to change configurations of the end effector, such as to open and close opposite jaws of the end effector. The effector sleeve can be a single unit in form of an electrically insulated sleeve extending the whole length from the end effector to the junction slider. The effector sleeve can also be operatively connected to the end effector slider via another tubular member, such as e.g. a coil member surrounded by an electrically insulating tube, or be operative connected to the end effector slider via an effector wire extending between the effector sleeve and the end effector wire inside a lengthwise extending channel.

Irrespective of how the effector sleeve is configured and connected to the end effector slider it is lengthwise displaceable by sliding the end effector slider to move the effector sleeve along the tube. This way the end effector can be alternating arranged in a sampling position, where the end effector is at least partly exposed from said effector sleeve, and a confined position, where the end effector is located at least partly inside the effector sleeve.

The junction slider serves to move the tube with the end effector surrounded by the effector sleeve out of the distal opening of the endoscope, thus to move the end effector in the desired position at the specific target site in preparation for resecting a tissue specimen. When the end effector slider is pulled towards the proximal guide end it retracts the effector sleeve and exposes the end effector, which opens the jaws of the end effector. Moving the end effector slider forward again towards the distal guide end pushes the effector sleeve forward to close the jaws around the tissue specimen.

So if the end effector is of the forceps kind having opposite jaws, said opposite jaws can be moved apart by operating the end effector slider, e.g. by pulling or pushing at the effector sleeve, e.g. by means of an effector wire extending between the end effector and the end effector slider, or by means of a reinforcing member, such as a reinforcing coil around the tube, any of which being secured at opposite ends to the end effector and the end effector slider, respectively.

In the position of the end effector where it is free of the effector sleeve, the jaws can grasp and cut off a tissue specimen by application of diathermy. When the jaws are to be closed again the end effector slider is operated to pull the end effector back again inside the effector sleeve. The tissue specimen is confined between the closed jaws.

In the alternative to reciprocating the effector sleeve the end effector can be reciprocated in and out of the effector sleeve.

When the end effector is fully, or substantially fully, inside the effector sleeve, the jaws of an end effector in form of a forceps is closed to define a closed biopsy cup. The effector sleeve effectively seals any gaps around the closed jaws of the end effector.

The effector sleeve may e.g. be a steel sleeve or be elastic. It may be preferred that the endosurgical device has a firm fit between an interior surface of the effector sleeve and the exterior surface of the tube to prevent liquid from flowing externally to the tube along a gap between said surfaces towards the slide rail assembly. In the alternative a gasket can be used as a seal against said surface of the tube. Such fit or sealing are of the kind that allows the effector sleeve to reciprocate along the tube. Typically the end effector and/or a further tubular member, which are used to couple the end effector and the junction slider in operative communication, are in sliding contact.

Advantageously a tubular member, such as a coil member that connects the effector sleeve with the end effector slider, may serve as the reinforcing member of the tube, so as to provide the endosurgical device with required stiffness and structure to be guided along the working channel of the endoscope without coiling or kinking. The effector sleeve can be made of a material that does not take away the bending properties of e.g. a bendable tube or tubular member, be a tubular member having insulation properties, etc. In embodiments having a long effector sleeve extending from the end effector to the junction slider the reinforcing member may serve as the effector sleeve. The reinforcing member may also be connected to the effector sleeve and move along the tube together with the effector sleeve.

In yet an alternative embodiment the effector sleeve can be connected to the junction slider by means of a wire, so that the effector sleeve can be displaced when the junction slider moves along the guideway.

The reinforcing member or other tube, such as a coiled member or spiral member, can thus be used around the tube to make it sufficiently rigid to be moved in and out of the working channel of the endoscope but still be bendable and maneuverable. When using e.g. a reinforcing spiral member or coiled member to add support to the tube, this member may advantageously be encapsulated by an exterior heat-shrink tubing or sheath. The heat-shrink tubing advantageously seals and insulates the endosurgical device along its length, e.g. to prevent it from letting out flushing fluid, but also to make it easy for the endosurgical device to be passed through the working channel due to low friction, and so that the tube cannot get in electrical contact with the working channel.

A distal end of the reinforcing member may be joined to a proximal end of the effector sleeve to combine the reinforcing member to the effector sleeve to allow the reinforcing member to move the effector sleeve along the tube to move the end effector in an out of the effector sleeve by operating the end effector slider. The exterior heat-shrink tubing or sheath may be used to combine effector sleeve and reinforcing member end-to-end.

The junction slider communicates with the first, the second and the third lengthwise extending channels inside the tube.

Liquid to flush the target wherefrom tissue specimens are to be resected and acquired is conveniently provided into the first lengthwise extending channel via a flow channel of the junction slider. Then diathermy is applied to the tissue by applying current from a diathermy generator to the end effector via the electrical wire in the third lengthwise extending channel. The electrical wire extends inside the third lengthwise extending channel of said tube and ends at the junction slider of the slide rail assembly.

In the alternative the function of the third lengthwise extending channel to guide the electrical wire can be obtained by one of the tube's other lengthwise extending channels, which other lengthwise extending channel then have dual function, and in which case the electric wire is insulated to not come into contact with fluid inside the other lengthwise extending channel.

In the embodiment utilizing an effector wire for operating the effector sleeve or the end effector, such an effector wire may be positioned in the first or second lengthwise extending channel.

An end effector may have opposite jaws pivotable arranged to diverge from a longitudinal axis of the end effector in a condition when the end effector is at least partly outside the effector sleeve so that the jaws can span a large tissue specimen. The jaws become closed when the end effector is retracted inside the effector sleeve or when the effector sleeve is moved forward to surround the end effector whereby the jaws define a closed biopsy cup. After application of diathermy the gently resected tissue specimen is confined between the jaws inside the biopsy cup, and the first lengthwise extending channel and the second lengthwise extending channel of the tube become in liquid communication at the distal tube end so that when the first lengthwise extending channel is flushed, or suction is applied to the second lengthwise extending channel, the tissue specimen is forced into the second lengthwise extending channel and delivered to the junction slider where said tissue specimen can be collected.

Two opposite diverging jaws of an embodiment of an end effectors may e.g. open about 5 mm so that large tissue specimens can be obtained, and due to using diathermy these tissue specimens taken using the endosurgical biopsy device of the present invention have clean cutting edges. Frying and burning of said edges are reduced, or even eliminated.

Besides facilitating application of resecting clean, rather large tissue specimens, by application of diathermy, another huge advantage is that the orientation of a resected tissue specimen is kept under control to a higher degree than in known biopsy procedures using know devices. A tissue specimen resected by application of diathermy can be kept confined between the jaws of the end effector in substantially same orientation as it is taken from the target tissue. The tissue specimen substantially fills the closed biopsy cup so that it cannot shift position. When a flushing liquid is injected under pressure to the first lengthwise extending channel from the junction slider, or suction applied to the second lengthwise extending channel, the tissue specimen is forced into the second lengthwise extending channel while keeping its orientation. So it is attempted that when the tissue specimen reaches the proximal end of the tube its orientation is still known. The tissue specimen can then be collected from the junction slider in a known orientation, thereby providing valuable diagnostic information of cellular architecture of the tissue specimen in view of having knowledge of the site specific origin and orientation of the tissue specimen. This improved ability to control orientation ensures a high level of specificity, highly reliable diagnosis and permits a facilitated assessment of the relevance of results in relation to clinical and anatomic normal and abnormal features of the target tissue.

The second lengthwise extending channel is selected to have a diameter that allows for gentle expelling and transfer of the tissue specimen by simple flushing, preferably under pressure, or suction, and so that the tissue specimen is not swirled around and looses orientation. By careful and correlated dimensioning of biopsy cup and diameter of the second lengthwise extending channel the possible movements of the tissue specimen can be restricted to a very high degree.

The junction slider is slidingly arranged in relation to the guideway to move the end effector at the distal tube end out of the working channel to meet the target tissue.

Known forceps devices on the market that use diathermy cause the tissue specimen to be destroyed by the heat, and that the tissue specimen stick between the opposite cutting edges of the opposite jaws, so that the tissue specimen has to be manually removed from the forceps. When using diathermy for the endosurgical device of the present invention the tissue specimen is not severely damaged because the tissue specimen so easily releases from the organ and from the jaws, which jaws advantageously can be insulated exteriorly, and optionally due to the instant cooling of the jaws initiated by the flushing fluid.

In some embodiment utilizing an effector wire, said effector wire may be the electrical wire that is used for supplying current to the end effector, in which case the electrical wire that extends inside the third lengthwise extending channel may optionally be associated with the end effector slider instead of with the junction slider. In yet an alternative the effector wire may be provided in a separate lengthwise extending channel of the multi-channel tube.

The slide rail assembly may advantageously further have a needle slider reciprocatingly disposed in the guideway in front of the junction slider at the proximal guide end, which needle slider may have a needle or a nozzle secured thereto, which needle or nozzle may be reciprocatingly arranged inside a fourth lengthwise extending channel of the tube between a first needle position in which the needle or nozzle is in a retracted position and a second needle position in which the needle or nozzle is exposed from the end effector, e.g. between open jaws of the end effector.

In the biopsy procedure the needle or nozzle may serve for application of e.g. a local anesthetic, other medicament or solution at one or more target sites or local areas, e.g. target sites or local areas wherefrom a tissue specimen is to be acquired by resecting. Injecting a liquid into the tissue areas to be resected expands said tissue area thereby displaying the tissue to both the fiber optics of the endoscope and offering the relevant tissue as an easy accessible target for the operator of the endosurgical device of the present invention to use and operate the end effector. This technology of expanding tissue prior to sampling has not been used extensively because it requires at least two additional insertions and retractions of instruments of the working channel of the endoscope per tissue specimen.

The jaws of an embodiment of an end effector of the present invention may in the closed configuration enclose the needle tip of the needle or the nozzle tip of the nozzle entirely. So when the biopsy cup is closed no parts of the nozzle or needle is outside said biopsy cup.

In an alternative embodiment of an end effector of the present invention one of the opposite jaws of the end effector has an opening configured to expose a needle or a nozzle when the jaws are closed. The opening may be closed and plugged sealingly by the needle or nozzle.

When the biopsy cup is closed after having been open, and the needle or nozzle having been exposed to apply anesthetics to the target, the needle or nozzle may reciprocate back inside the fourth lengthwise extending channel of the tube so that the jaws can be closed.

The endosurgical device of the present invention can however also advantageously be used without general anesthesia, e.g. on an out-patient or on a patient at the receiving ward. The surgeon may take his decision as to anesthesia at any stage during the biopsy procedure without causing the patient inconvenience. The endosurgical device allows the surgeon to take various choices and to take several tissue specimens directly from the suspicious target area without having to repeat inserting a series of different tools into the working channel of the endoscope for each choice and resecting of a tissue specimen. Cancer cells can be destructed by application of diathermy while the endosurgical device is still inside the patient. The patient can go home immediately afterwards, needs no catheter, nor fasting before the surgical biopsy procedure.

The junction slider may have at least one of
an inlet port in fluid communication with the first lengthwise extending channel for delivering a flushing liquid at and/or to the end effector,
a diathermy port in communication with the third lengthwise extending channel, and/or
a sample port in communication with the second lengthwise extending channel for coupling with a tissue specimen collector, and/or for removing matter from the biopsy site, and/or for transferring matter confined within the end effector or held by the end effector out of the endosurgical device.

Within the context of the present invention the term "proximal" means closest to something and the term "distal" means farthest from something. As an example the proximal tube end is the end closest to the operating end of the endoscope when in use, and the distal tube end is the end closest to the tip of the operating part of the endoscope. The terms "proximal" and "distal" are used in context of this orientation throughout the application text.

A reservoir of flushing liquid can easily be connected to the inlet port of the junction slider in various ways. One way is to insert into the inlet port a stepped tapered connector coupled to a liquid supply tube, in which case the inlet port serves as a female coupling component. Instead the liquid supply tube can be mounted on the inlet port, in which case the inlet port serves as a male coupling component.

The electrical wire may extend out of the second lengthwise extending channel at the proximal tube end and into the diathermy port to create an electrical contact to the diathermy generator. Such electrical contact can be obtained in a very simple manner by inserting an electrical plug of a cable that goes to the diathermy generator.

The junction slider may also have a sample port that by means of being in communication with the second lengthwise channel allows resected tissue specimens to be conveyed from the biopsy cup, through the tube and out of the slide rail assembly for diagnosis. A tissue specimen can simply be flushed out of the sample port by flushing liquid through the first lengthwise extending channel into the closed biopsy cup to push the tissue specimen in fixed orientation into the second lengthwise extending channel. If the first lengthwise extending channel that is used as the delivery channel for the flushing fluid also is used as the third lengthwise extending channel, the electrical wire must be insulated. In the alternative suction can be applied to the second lengthwise extending channel to convey the tissue specimen along said channel.

The second lengthwise extending channel may have a larger cross-section than the first lengthwise extending channel to inherently further promote ejecting the tissue specimen by flushing or suction. Preferably the second lengthwise extending channel may have the largest cross-section possible in view of the dimensions of the other lengthwise extending channels and the overall diameter of the tube, so that the tissue specimen is treated as gently as possible during its travel out and free of the tube, but without the tissue specimen can swirl around inside the second lengthwise extending channel and shift orientation.

Tissue specimens should be deep enough to include both lamina propria and muscularis mucosae, i.e. 3-5 mm in depth. The tissue specimen will automatically be pushed by the pressure of the flushing fluid of the first lengthwise extending channel towards the larger or same cross-section of the second lengthwise extending channel. The tissue specimen is pressed into and along said second lengthwise extending channel by the flushing fluid or the applied suction because the second lengthwise extending channel is the only channel that allows the tissue specimen to slip inside and pass along with the flushing fluid out of the outlet of the sample port. When the tissue specimen is subjected to the pressure or suction of the flushing fluid it may conform slightly to the lumen of the second lengthwise extending channel as regards shape to pass the easiest through said second lengthwise extending channel.

The end effector slider, the junction slider, and/or the needle slider can in an expedient embodiment reciprocate along the guideway of the main slide guide body of the slide rail assembly. In such a configuration of the slide rail assembly the needle or nozzle can extend from the proximal tube end through the junction slider to be connected to the needle slider, whereby the slide rail assembly can be constructed with minimum size. In the alternative the needle or nozzle runs in the third lengthwise extending channel parallel to and outside the junction slider. Within the scope of the present invention the junction slider and the needle slider can be arranged in parallel instead of in series, in which case however the proximal end of the needle or nozzle needs to be bend away from the longitudinal axis of the slide rail assembly at its exit from the proximal tube end for being secured to the needle slider. A parallel arrangement of the junction slider and the needle slider makes the slide rail assembly more voluminous, which might obstruct and affect the surgeon's maneuverability of endoscope and endosurgical device. The center axis of the third lengthwise extending channel is radially offset the center axis of the tube which places the needle radially offset the center axis of the tube as well. In fact the needle may be provided very close to the circumferential main wall of the tube.

The slide rail assembly may further have a first spring member located between the end effector slider and the junction slider for spring-biased reciprocation of the end effector slider against the junction slider. The slide rail assembly may further or additionally have a second spring member located between the junction slider and the needle slider for spring-biased reciprocation of the needle slider against the junction slider. Alternative arrangements that temporarily can keep the sliders under tension or compression in relation to each other are within the scope of the present invention. Such arrangements could be co-operating indents and beads, or manually operated reciprocatable pins that e.g. extend crosswise the guideway in front of a distal end of a slider or engaging a slider, etc.

At the storage state and during inserting the endosurgical device into the working channel of the endoscope none of the spring members may be biased. Once the distal end of the endoscope is in position at the suspicious-looking tissue target the endosurgical device and the patient is ready for biopsy and the endosurgical device is prepared for resecting the tissue specimen by inserting the tube in the working channel such that a tissue specimen optically detected using the fiber optics of the endoscope can be resected. The junction slider is operated to move the end effector out of the endoscope. Then the end effector slider is operated to retract the effector sleeve thereby allowing opposite jaws of the end effector to get apart to span and grasp a tissue specimen. To expose the distal tube end with the end effector and effector sleeve from the endoscope's distal opening, the junction slider travels in the guideway without compressing the spring members. If anesthetics are needed at the biopsy site the needle slider is moved forward towards the junction slider thereby compressing the second spring member.

Spring-biasing the needle slider by compression of the second spring member reduces the risk is eliminated that the end effector is retracted inside the effector sleeve while the needle or nozzle is still in its forward exposed position.

The compression of at least the second spring member may also contribute to that the jaws do not breaks inside the organ by accident by accidentally closing around an exposed needle. The needle will automatically retract when compression force is relieved.

As a further safety precaution the spring members can advantageously be compression springs, such as coils, having different numbers of coils per unit length, and optionally also one or more different parameters selected from different coil diameter and different wire thickness, in order to be loaded to a different compression, e.g. so that the second spring member springs back faster than the first spring member upon release of compression and load on said spring members. As already mentioned above this arrangement of spring members provides safety against the end effector accidentally and unintentionally closes prior to the needle or nozzle has been pulled inside the biopsy cup again. A suitable structural and functional precaution to prevent the end effector from catching the exposed needle or nozzle can thus simply be facilitated by configuring the second spring member with a larger compression force than the first spring member whereby the second spring member retracts the needle slider faster than the first spring member is relieved of the compression force between the end effector slider and the junction slider.

The sliders of the slide rail assembly can be operated manually and hold on to by the surgeon. This may however be a somewhat clumsy way to operate the slide rail assembly, and not safe and reliable. A safer and more practical way to operate the end effector via the slide rail assembly can be a remote actuator assembly having a remote operating handle with buttons allocated to operating the respective sliders and functionalities, and being operatively connected to the sliders via respective operating strings. The operating strings can e.g. be wires, such as metal wires, but any kind of string having same strength and similar ability to bend and flex without rupturing can be used within the scope of the present invention. Strong polymeric strings, such as e.g. fiber reinforced strings, are examples of alternative to metal wires.

The remote actuator assembly may comprise a sheave assembly, which sheave assembly can be located at the junction slider to move together with said junction slider in response to pulling an operating string by operating a respective button of the remote operating handle. The operating string may loop around the sheaves of the sheave assembly one or more times. The more times the larger mechanical advantage can be obtained. A small stroke of a button can thus cause a longer displacement of a slider.

To operate the slide rail assembly by means of the buttons of the remote operating handle, said remote actuator assembly may expediently include
  a first operating string having a first proximal string end secured to the end effector slider and an opposite first distal string end secured to a trigger button of the remote operating handle to operate the effector sleeve to open and close opposite jaws of said end effector, or vice versa,
  a second operating string having a second distal string end secured to a distal guide end of the tubular guide housing of the main slide guide body, which second operating string runs around a first track of the sheave assembly, preferably through a tube guide, via a fixed point at a wheel button of the remote operating handle and returns from the wheel button, preferably through the tube guide, to the proximal end of the tubular guide housing of the main slide guide body via a second track of the sheave assembly to have a second proximal string end secured to a proximal guide end of the tubular guide housing to move the effector sleeve lengthwise in relation to the end effector, and
  a third operating string having a third proximal string end secured to needle slider, and an opposite third distal string end secured to a slider button of the remote operating handle to move the needle slider, and thus exposing the needle from the end effector.

All of the first, second and third operating strings may advantageously run inside the same guide tube, such as a Bowden conduit, that guides the operating strings towards and inside the remote operating handle in combination. The sheave assembly and the guide tube are optional, although preferred.

A further advantageous feature of the remote operating handle is that the remote operating handle can have a snap-on means for displaceable and detachable attachment of said remote operating handle to the distal part of the endoscope, such as the flexible part of an endoscope, whereby said remote operating handle is easy at hand of the surgeon at all times during the biopsy procedure. The remote operating handle can be snapped-on/snapped off the distal tube part of the endoscope both in parallel of perpendicular as the surgeon or operator prefers, and slide along said distal tube part.

If the surgeon prefers so he/she can detach the remote operating handle from the distal part of the endoscope to operate the slide rail assembly in any of his/her preferred positions. He/she can also slide the remote operating handle lengthwise along the distal part, or temporarily store the remote operating handle when not in use so that it is not in the way at the proximal end of the endoscope. The remote operating handle of the present invention gives the surgeon more ergonomic operating conditions and eliminates the need for some of the additional staff needed during a conventional endoscopic biopsy procedure. In the context of the present application the term "remote" means separated by a distance from the slide rail assembly, which distance is provided by the guide tube, for the endosurgical device to be operated without directly touching the slide rail assembly and/or at a distance from said slide rail assembly.

Prior to resecting the tissue specimen the patient is prepared for the biopsy. Such preparation can sometimes include flushing an irrigant, such as a saline solution, through the endoscope or through the endosurgical device, to rinse or optionally expand the organ or body cavity. If the organ is the urinary bladder a cystoscope may be used and the bladder be inflated with the saline solution to rinse the urinary bladder to a level that gives a clear vision of the urinary bladder wall. The organ or body cavity may typically be emptied of any electrically conductive flushing/rinsing solution prior to tissue acquisition by diathermy. The flushing/rinsing solution can be collected for histology and diagnosis of pathologies.

Saline solutions are the typical irrigant solution. Saline solutions are however conductive and therefore not compatible with diathermy. So the saline solution is replaced with a non-conductive flushing solution, e.g. a glycine solution, a solution of other non-conductive amino acids, or a sugar solution such as e.g. a mannitol solution. A glycine solution, of e.g. 1.5%, can be used as flushing solution instead of saline during diathermy, and for distending the organ in preparation for biopsy.

The device operating part may further comprise a flushing component having a first operating end part adapted to be mounted to an endoscope fluid valve port and to an endoscope suction valve port of an endoscope, and an opposite second operating end part adapted to couple to the slide rail assembly and to the endoscope at or in the vicinity of the instrument port of the endoscope.

Initially the organ or tissue site may be rinsed using a saline solution and the conventional procedure and suction/flushing channel of the endoscope.

Alternatively the flushing component may initially be used for the same purpose as a shunt bypassing the proximal parts of the suction channel and the liquid channel of the endoscope between the fluid valve port and the suction valve port and the instrument port, to make liquid flow via the instrument port instead, and out of the distal end of the associated channel of the endoscope thereby flushing the organ or tissue site of interest via e.g. the working channel and the tube, and evacuate infused liquid again in a later step via the endoscope or the tube, thereby rinsing the organ prior to biopsying and being able to collect evacuated flushing solution.

The opposite second operating end part may conveniently be adapted to be coupled to the instrument port of the endoscope device operating part via an adaptor coupled to the instrument port. In the alternative the adaptor is an integral part of the second operating end part.

The adaptor may include a tubular adaptor body that has a first adaptor end part with a first adaptor end, and an opposite second adaptor end part with a second adaptor end. The first adaptor end part may be dimensioned to replace the end cap of the instrument port, preferably including a membrane for introduction of the tube of the endosurgical device. The second adaptor end part may be configured for coupling with the slide rail assembly and holding the slide rail assembly together with the endoscope at the instrument port.

The first adaptor end part and the second adaptor end part may be at an angle in relation to each other, so that the slide rail assembly is directed at least slightly away from the longitudinal axis of the endoscope and thereby being highly accessible and operational by the surgeon. The first adaptor end part may conveniently be configured similarly as the instrument port of the endoscope with a membrane through which the tube of the endosurgical device of the present invention can be inserted into the working channel of the endoscope, enabling liquid to be supplied into the first lengthwise extending channel and leave via the second lengthwise extending channel.

Preferably the adaptor can also rotate in the instrument port, such as at least 45°, about a central axis of the endoscope's instrument port, to further provide improved operating conditions for the surgeon or other operator. In the alternative the slide rail assembly can rotate in relation to the adaptor in a similar manner about a central axis of the endoscope's instrument port, to thereby also rotate the end effector.

Establishing fluid communication between one or more of liquid reservoirs, containers for collecting discharged matter, the first and second lengthwise extending channel of the tube, and the junction slider of the slide rail assembly requires tubes there-between. It may thus be expedient if the adaptor has seats for coupling pieces for mounting one or more tubes to one or more of the components selected from the group comprising one or more pump means, a liquid reservoir, a drainage reservoir, the inlet port of the junction slider, the sample port of the junction slider, an inlet port to a tissue specimen collector secured to the sample port or an outlet from the tissue specimen collector secured to the sample port, to obtain liquid communication and flow channels between respective such parts and keeping control of the tubings so that these are not in the surgeon's way when he/she operates the endosurgical device to acquire tissue specimens.

A tissue specimen collector may be a multi-chamber collector for directly collecting a resected tissue specimen in a dedicated chamber upon exit of the sample port, and for accommodating the tissue specimens in the order they are resected, preferably collecting the tissue specimen in a known orientation in the dedicated chamber in view of the orientation at the target site wherefrom the tissue specimen is taken. Within the scope of the present invention the term "dedicated chamber" means that a tissue specimen has its own chamber. The terms "chamber" and "dedicated chamber" are used herein interchangingly in the context of the collector rack.

To collect tissue specimens one after another in dedicated chambers the tissue specimen collector may comprise a main collector housing, a collector rack with a series of adjacent chambers for accommodating tissue specimens, and means for moving the collector rack lengthwise along the longitudinal axis of the main collector housing to position said dedicated chambers one after another below the sample port of the junction slider, thereby in a simple manner corresponding the order that the tissue specimens are resected to the order that the dedicated chambers are arranged below the sample port of the junction slider. Once a dedicated chamber has been filled with a tissue specimen a new dedicated chamber is moved in liquid communication with the sample port ready to receive the next tissue specimen. This procedure is continued until the full tissue specimen sampling map has been completed, in which case all dedicated chambers typically are filled. The collector rack may however have extra channels. For a urinary bladder biopsy the collector rack may have seven or more dedicated chambers.

The dedicated chambers may be sized and dimensioned so that once a tissue specimen is arrived and accommodated in said chamber, said tissue specimen cannot move around. Since the tissue specimen has little opportunity to shift orientation during its travel out of the biopsy cup, along the second lengthwise extending channel, and out of the sample port the risk that the tissue specimen change orientation is substantially reduced compared to conventional techniques, where the surgeon's assistant simply collects the tissue specimens one after another, and manually places them in separate, labeled vials where the tissue specimen flows around.

Using the tissue specimen collector of the present invention only one labeling action is required in that all tissue specimens from one procedure are collected in a single cassette or cartridge, namely the collector rack, that inherently informs of the biopsy site, e.g. by having patient ID, a number or other information that allocates a tissue specimen in a dedicated chamber to a site on the biopsy procedure map. The entire collector rack can be send directly to histology analysis.

The means for moving the collector rack lengthwise along the longitudinal axis of the main collector housing may simply be a screw rod with an exterior thread, which screw rod serves to be screwed deeper and deeper inside a threaded hole or bore in the collector rack, or vice versa, thereby carrying the collector rack along, e.g. away from the distal guide end of the main slide guide body. The screw rod may have a knob at a free end facing away from the collector rack, which knob is rotated to screw the rod in and out of the hole or bore. Other arrangements to stepwise, and in sequence, fix the position of the dedicated chambers of the collector rack below the sample port of the junction slider may be a ratchet mechanism, or opposite male/female engaging components at suitable distances along the collector rack and main collector housing.

The main collector housing may have a collector port for fluidly coupling to the sample port of the junction slider, optionally via a coupling piece extending between the sample port of the junction slider and the collector port of the main collector housing, and a liquid outlet to discharge liquid entering the main collector housing via the coupling piece from the sample port, thus from the second lengthwise extending channel during ejecting of the tissue specimen from the biopsy cup by flushing. A dedicated chamber of the collector rack can thus easily be aligned with the coupling piece coupled to the sample port to catch and receive a tissue specimen in said chamber. Surplus of liquid used to force the tissue specimen out of the second lengthwise extending channel, through the sample port, and via the coupling piece into a chamber of the collector rack, can flow out of the tissue specimen collector via the liquid outlet to be collected in a reservoir or container of any suitable kind, optionally for further histological analysis or safe depositing or safe discharge.

The collector rack may expediently be configured to allow liquid to pass through, e.g. by having a plurality of through-holes or canals extending from inside a chamber to the exterior of the collector rack and/or through-openings that extend through common walls of adjacent chambers and through exterior walls of the collector rack. In another embodiment the collector rack can be made of a filtering material, be porous, or having interstices through which liquid may pass into the main collector housing and out through the liquid outlet of the main collector housing, e.g. to be collected in a reservoir.

The opposite jaws of an end effector of the forceps kind may be obtained from two lengthwise pipes sections subsequently joined partly lengthwise and having jaws deflected from the lengthwise longitudinal axis of the end effector to confer an inherent resiliency to said jaws that will make the jaws to spring apart when the effector sleeve does not keep the jaws closed. Any of the end effectors described in the applicant's Swedish patent application no. 1751639-4 filed 22 Dec. 2017 and the applicants international patent application PCT/SE2018/051315 filed 14 Dec. 2018 can be part of the endosurgical device of the present invention. The disclosure of the end effectors described therein is incorporated by references in the present application.

The biopsy cup can be opened and then closed sealingly by the reciprocating movement of the effector sleeve induced by the reciprocating movement of the end effector slider to prevent flushing fluid from escaping the closed biopsy cup, and thus loosing flushing pressure, thus to substantially prevent flushing fluid from flowing into the organ or out to the biopsy site via crevices and/or gaps between opposite closed jaws when a tissue specimen is flushed out of the closed biopsy cup.

The exterior diameter of the tube may be as little as less than or equal to 2 mm for the endosurgical device to fit moveably inside a working channel of a cystoscope once a heat-shrink insulated reinforcing coil is put around the tube. However other kinds of endoscopes may have larger working channels, in which case the overall exterior diameter of the tube with enclosures can be as wide as about 2.5 mm, 3 mm, 3.5 mm, 4 mm, 4.5 mm, or even about 5 mm or above. The interior diameter of any of the lengthwise extending channels is smaller than the overall interior tube diameter, as measured as the largest distance between the lumens of the lengthwise extending channels.

The flushing pressure of the flushing liquid may be set in view of the diameter of the lengthwise extending first and second lengthwise extending channels of the tube and the size of the tissue specimens, as defined by the jaws of the end effector and of the closed biopsy cup, so that the tissue specimens are not trapped inside the second lengthwise channel, thereby avoiding and/or preventing plugging of said second lengthwise channel. For an endosurgical device that implements a tube of an exterior overall diameter of 2 mm for all functionalities, and being intended for use with a cystoscope, a rather high flushing fluid delivery pressure through the second lengthwise channel of at least 5 bar could be needed. The fluid delivery pressure may however be as high as 10 bar, or 20 bar, or even higher. A fluid delivery pressure of e.g. 26 bar has been demonstrated to be satisfactory and efficient. Similar suction levels can be used for same purposes.

The free opposite edges of cup-shaped second ends of the jaws form conductive pinching surface for contacting the tissue in application of diathermy when the jaws are moved towards each other by pulling at an effector wire or moving the effector sleeve so that the end effector is closed and arranged inside the effector sleeve.

Diathermy remedies the need for the surgeon to pull at the end effector extensively to mechanically resect the tissue specimen. The need for hemostasis by heat application subsequent to resection of the tissue specimen is highly reduced or even eliminated. The surgeon only has to wait a few seconds for the applied heat to set the tissue specimen free at very little discomfort to the patient and with minimum steps for the surgeon. Once the tissue specimen is set free, a force applied to the effector sleeve can make the biopsy cup to close fully. Alternatively the jaws can be proactively closed by means of the effector wire coupled to the end effector slider. Once the end effector has been closed the flushing liquid can pass through it without the biopsy cup leaks noticeably to loose flushing pressure, or without loosing suction. The tissue specimen is collected in a dedicated chamber of the tissue specimen collector and the tissue specimen can be brought to the analyst in a closed environment. No human contaminating interaction is needed to move the tissue specimens out of or from the organ and collect it into vials, such as a conventional vial. Contamination risk is zero from sampling to collecting, and mixing of tissue specimens is eliminated.

The jaws pinch the tissue specimen when the effector sleeve is moved forward by the end effector slider, and in the diathermy step the jaws gently sever the tissue specimen from the organ by diathermy, and sear and/or cauterize the wound left at the biopsy site to stop bleeding. In this manner the tissue specimen releases from the organ and do not stick to the jaws. The tissue specimen becomes freely accommodated and protected between the jaws inside the biopsy cup defined by the closed jaws when the end effector is inside the effector sleeve. The effector sleeve presses and holds the jaws tight together to close the biopsy cup around the tissue specimen in a substantially leak-proof manner and with the tissue specimen in a specific orientation that typically is not altered after the tissue specimen has been resected.

The exterior faces of the opposite jaws may be electrically insulated exteriorly to constitute a diathermy device that allows the tissue specimens to release from the organ. Electric insulation of the exterior faces of the jaws may preferably be obtained by providing a coating to said exterior surfaces. Such coating may preferably be a low friction coating, e.g. a Parylene® coating or a coating of Diamond-like carbon (DLC) that easily can be deposited on a conductive surface of the jaws, such as a metal surface, the metal being e.g. nitinol, aluminium or stainless steel. The trade name Parylene® covers chemical vapor deposited poly(p-xylylene) polymers often used as moisture and dielectric barriers. Within the scope of the present invention other kinds of insulating coatings can also be used.

The tube may be a non-conductive tube, such as a plastic tube. Preferably the organ is the urinary bladder, but other organs can be subjected to same dissecting principles, collecting principles and biopsy procedure, e.g. can the organ be the digestive tract, such as the intestine, stomach or esophagus; or the airways, such as the lungs; or the vagina.

If excess bleeding occurs diathermy can be repeated locally. The diathermy may be monopolar.

The needle or nozzle associated within the third lengthwise extending channel may be utilized for other purposes than anesthesia, such as for delivering expanding fluid to an organ or tissue site, inject medication, such as local anesthesia or adrenaline to stop bleeding. Other options include but are not limited to using a surgical laser or a clamp tool through the fourth lengthwise extending channel.

The steps of the surgical procedure using the endosurgical device of the present invention for taking tissues specimens may comprise the steps of a) inserting an endoscope, preferably an endoscope having means to visualize the organ internally, such as a fiber optic means,
b) optionally expanding the organ wherefrom tissue specimens are to be resected with liquid supplied through the working channel or other channel of the endoscope,
c) inserting the tube of the endosurgical device according to any of the preceding claims 1-19 into the working channel of the endoscope, optionally if not performed in step b) expanding the organ wherefrom tissue specimens are to be resected with non-conductive liquid supplied through a lengthwise extending channel of the endosurgical device,
d) optionally anesthetizing all areas suspect of cancer, or optionally anesthetizing locally at the sampling site, by operating the needle or nozzle of the endosurgical device via the needle slider, optionally inducing swelling to facilitate taking the tissue specimen,
e) exposing from the working channel of the endoscope the distal end of the tube, in a state where the effector sleeve surrounds the end effector, by operating the junction slider,
f) displacing the end effector and the effectors sleeve in relation to each other by operating the end effector slider, thereby opening and closing the jaws of the end effector to pinch a tissue specimen,
g) activating diathermy via the diathermy wire of the junction slider to provide current to the end effector to set the tissue specimen free for accommodation inside the biopsy cup,
h) from the junction slider flushing non-conductive liquid under high pressure into the first lengthwise extending channel and further into the closed biopsy cup of the end effector to flush the tissue specimen out of the tube via the second lengthwise extending channel of the tube, which second lengthwise extending channel ends at the junction slider, and collecting the tissue specimen at the proximal tube end, preferably collecting the tissue specimen in a formalin-containing vial or in a tissue specimen collector, optionally the tissue specimen collector defined in any of the preceding claims,
i) repeating steps e)-h) in case of anesthetizing all areas suspect of cancer have been anesthetized, or in case of local anesthesia repeating steps d)-h) until the relevant number of tissue specimens has been taken,
j) optionally destroying any remaining areas of cancer by burning function by moving the jaws to the tissue being destroyed,
k) withdrawing the endosurgical device, and
l) withdrawing the endoscope.

Step j) can be conducted at any stage of the biopsy procedure, and in fact since the same endosurgical biopsy device is used during one inserting of the endosurgical device in the working channel of the endoscope any desired steps can be conducted and repeated in accordance with the surgeons choice without removing the endosurgical biopsy device from the working channel. Thus the order of the steps indicated in the surgical procedure should not be construed af limiting and mandatory.

The invention will now be described below with reference to the drawing by way of an exemplary embodiment of an endosurgical device of the present invention.

Figure 5:
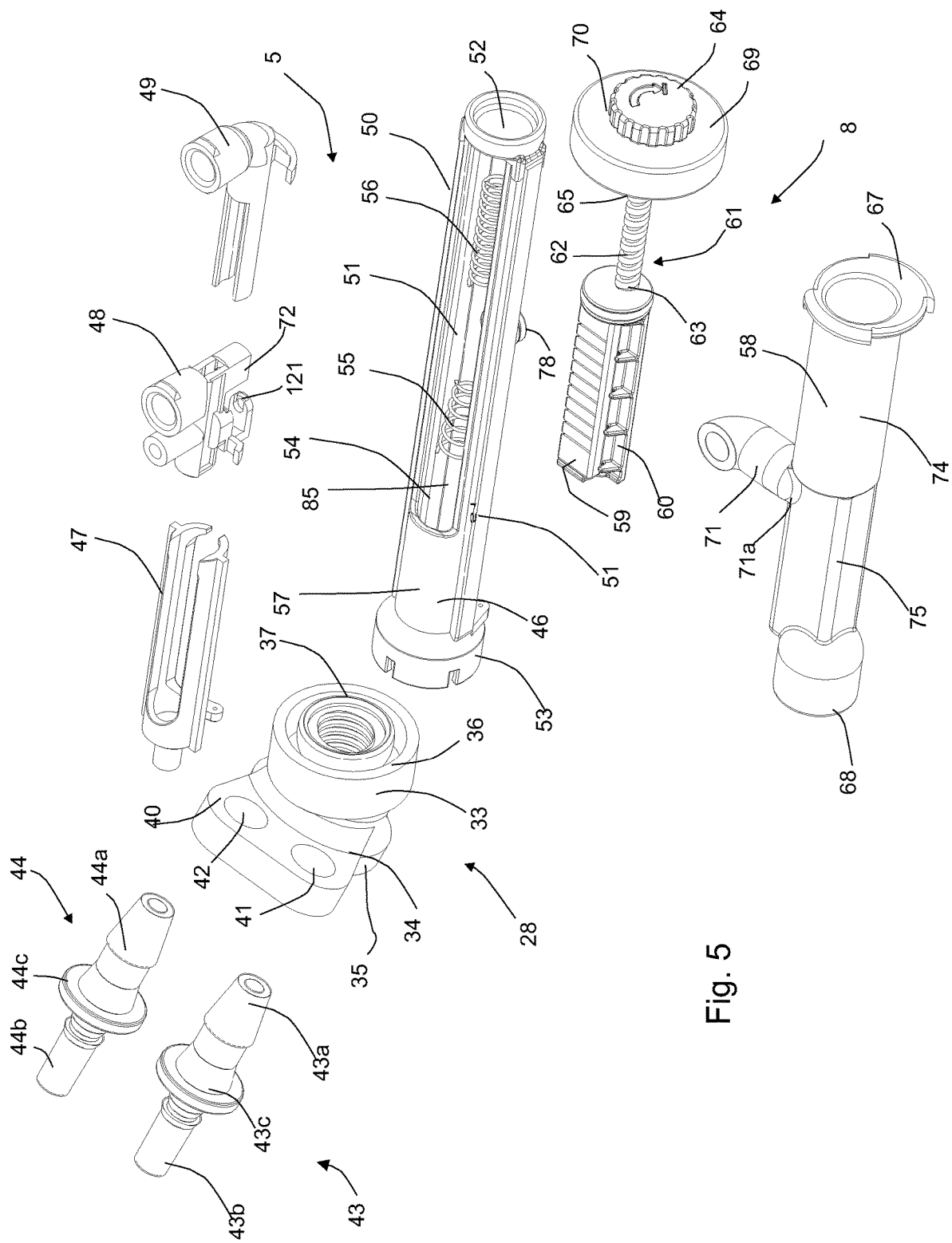
Figure 6:
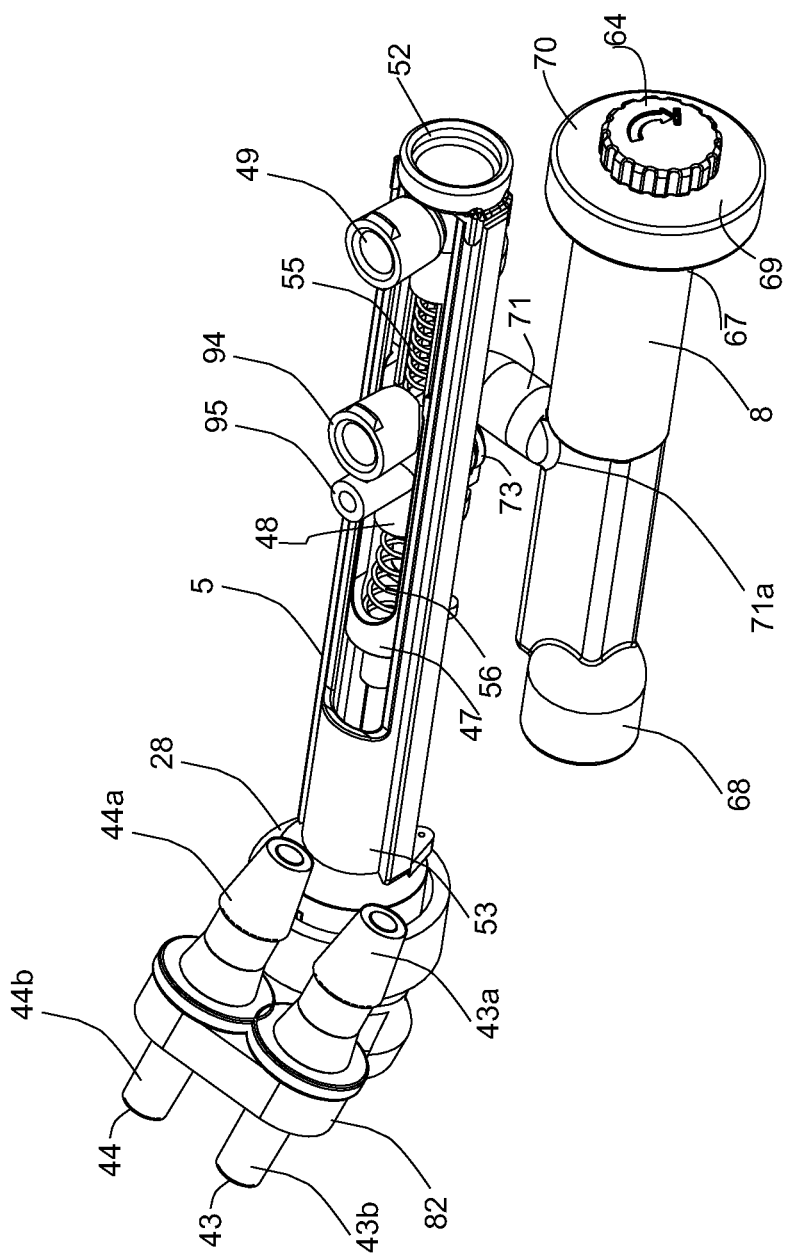
Figure 7:
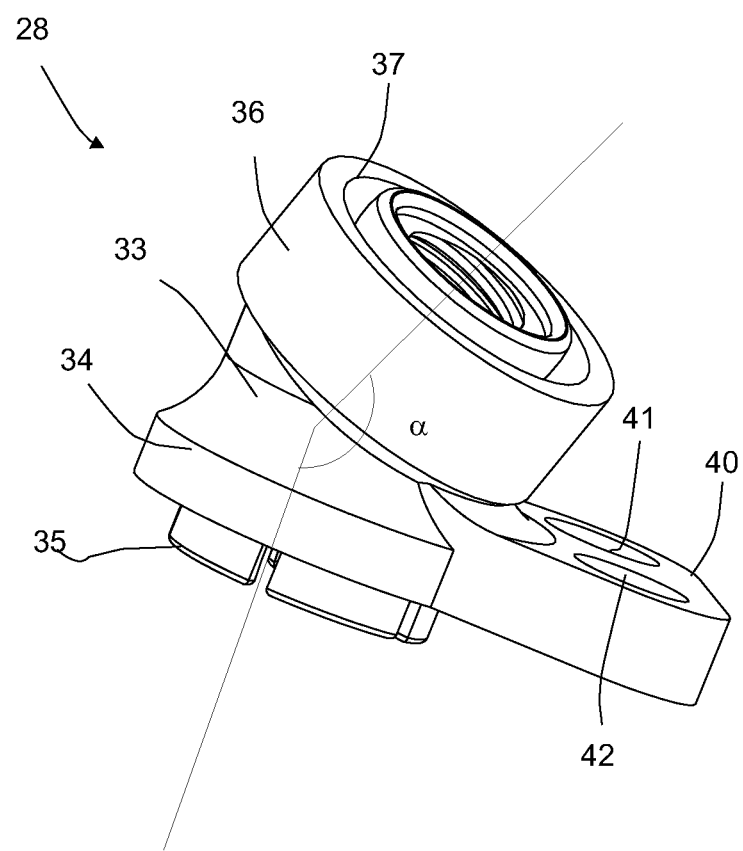
Figure 8:
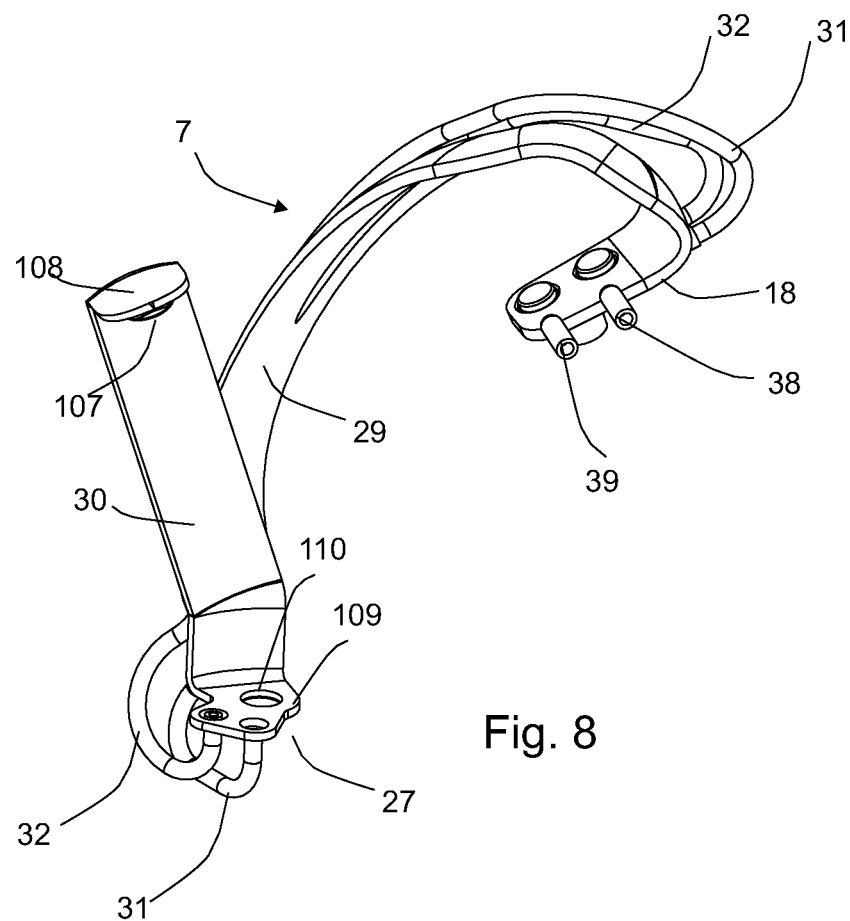
Figure 9:
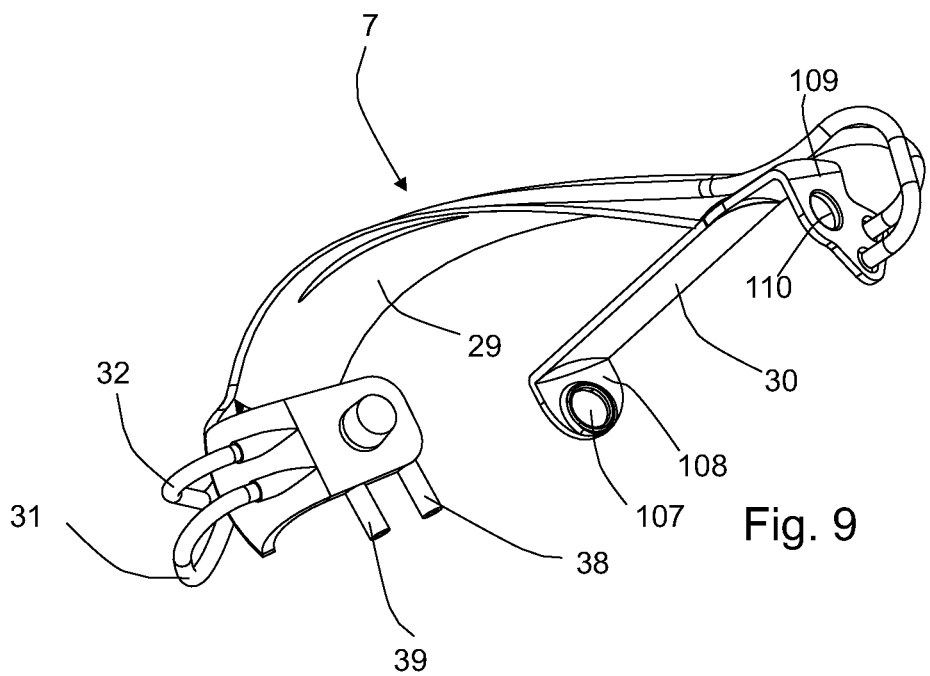
Figure 10:
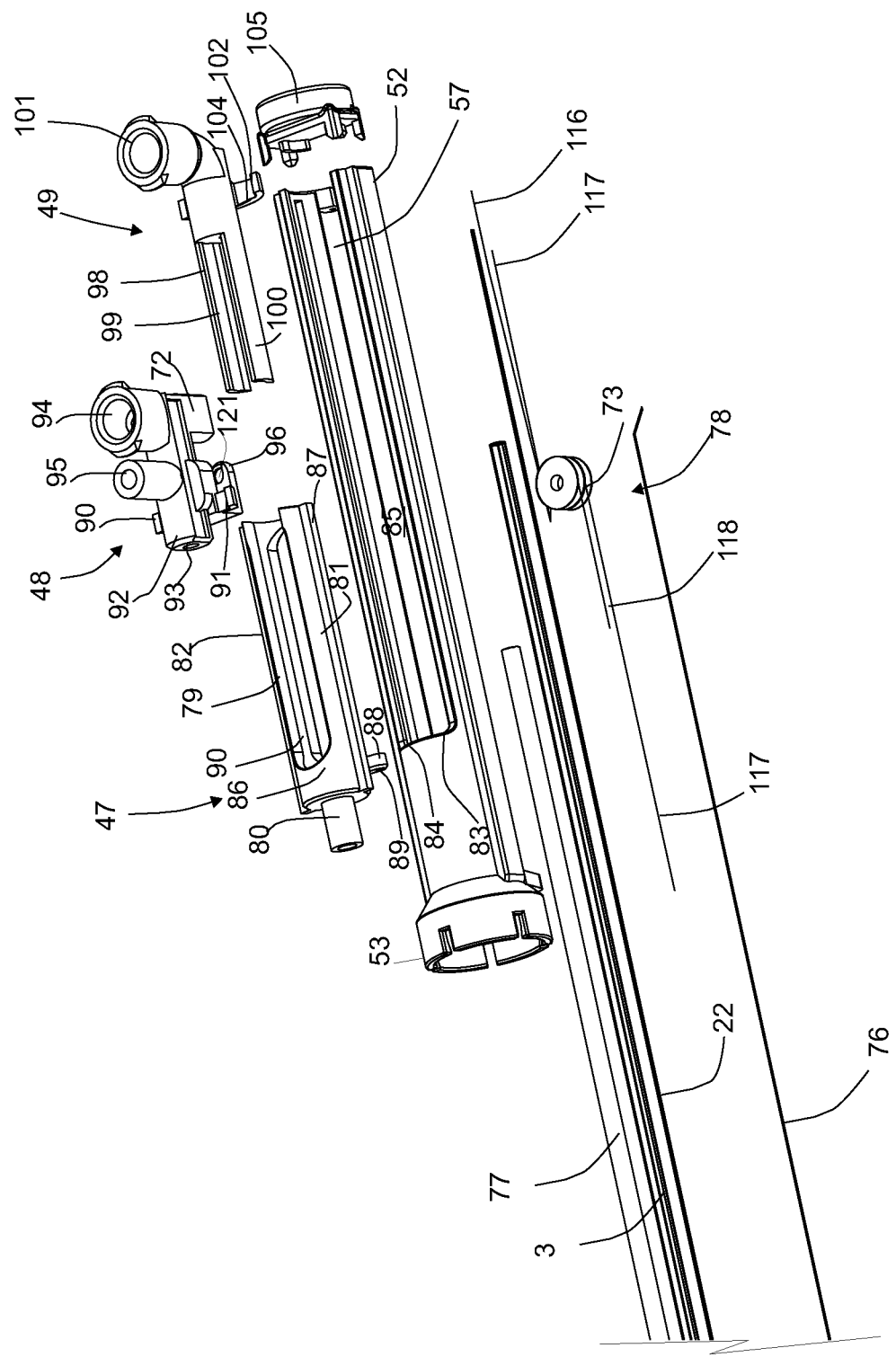
Figure 11:
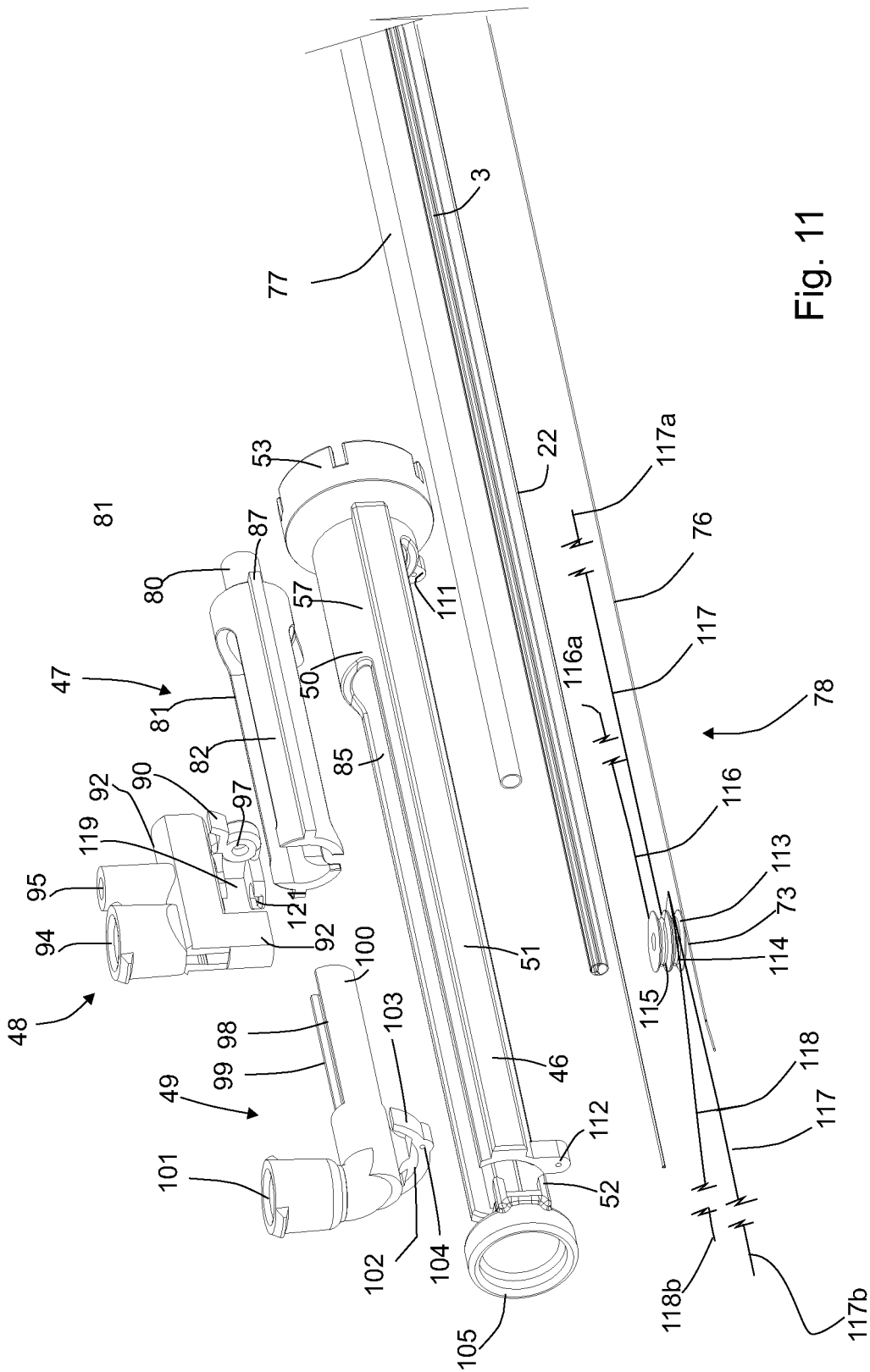
Figure 12:
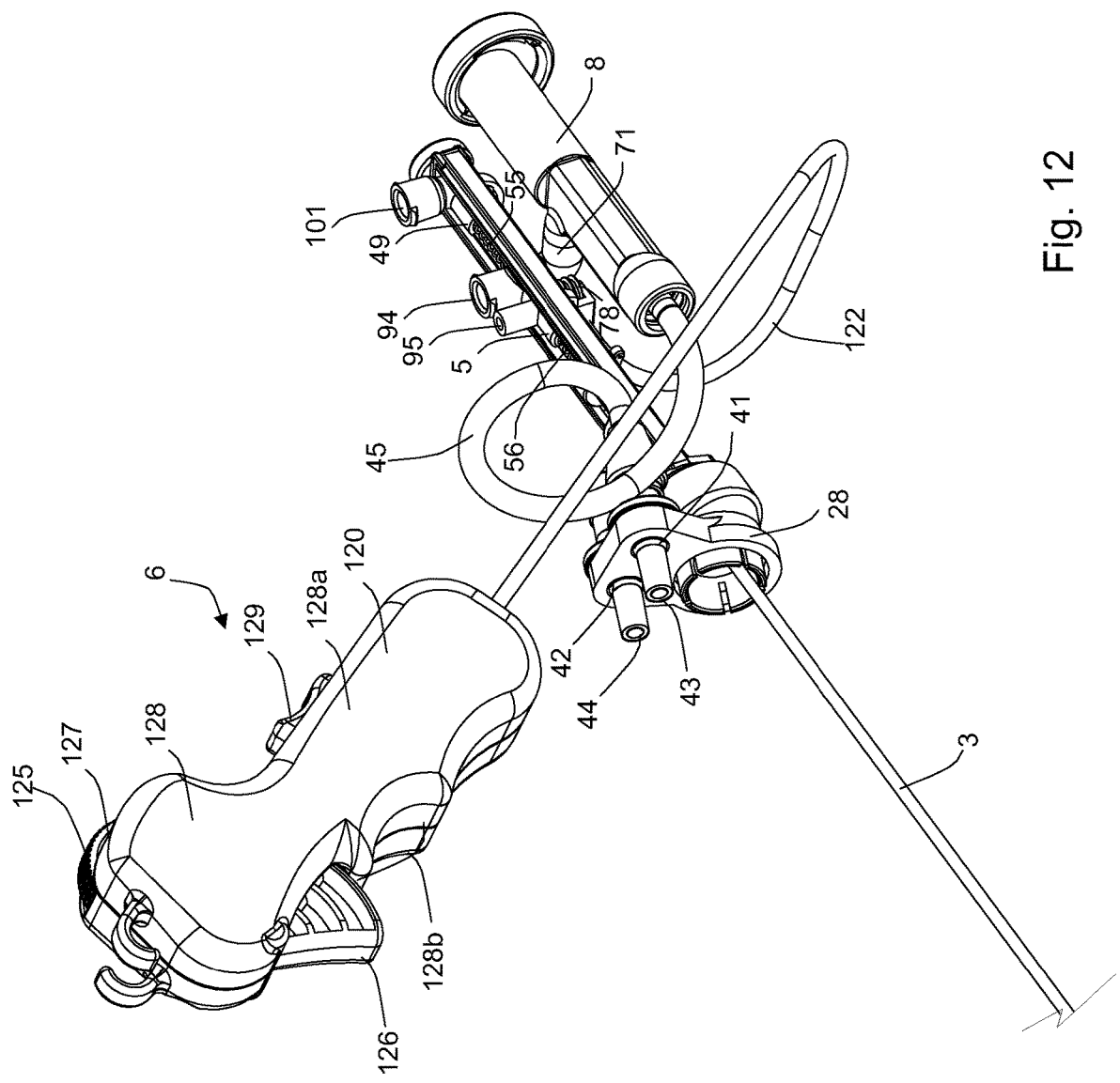
Figure 13:
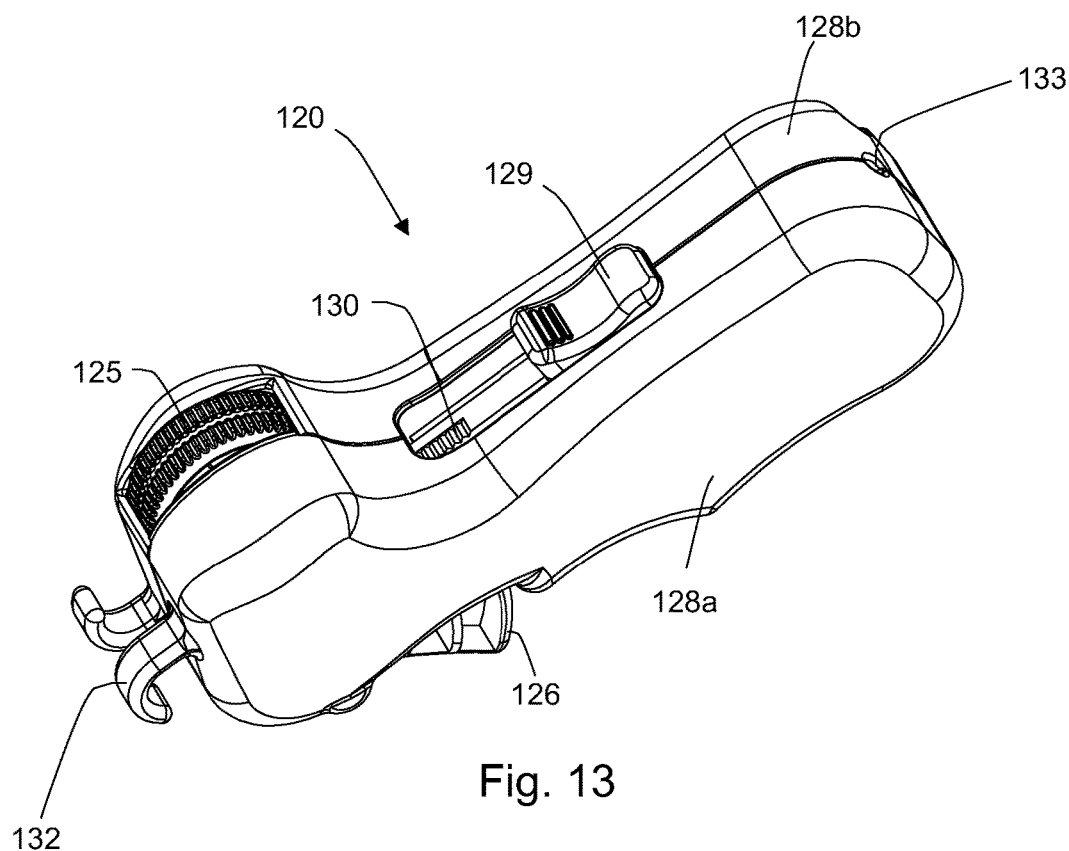
Figure 14:
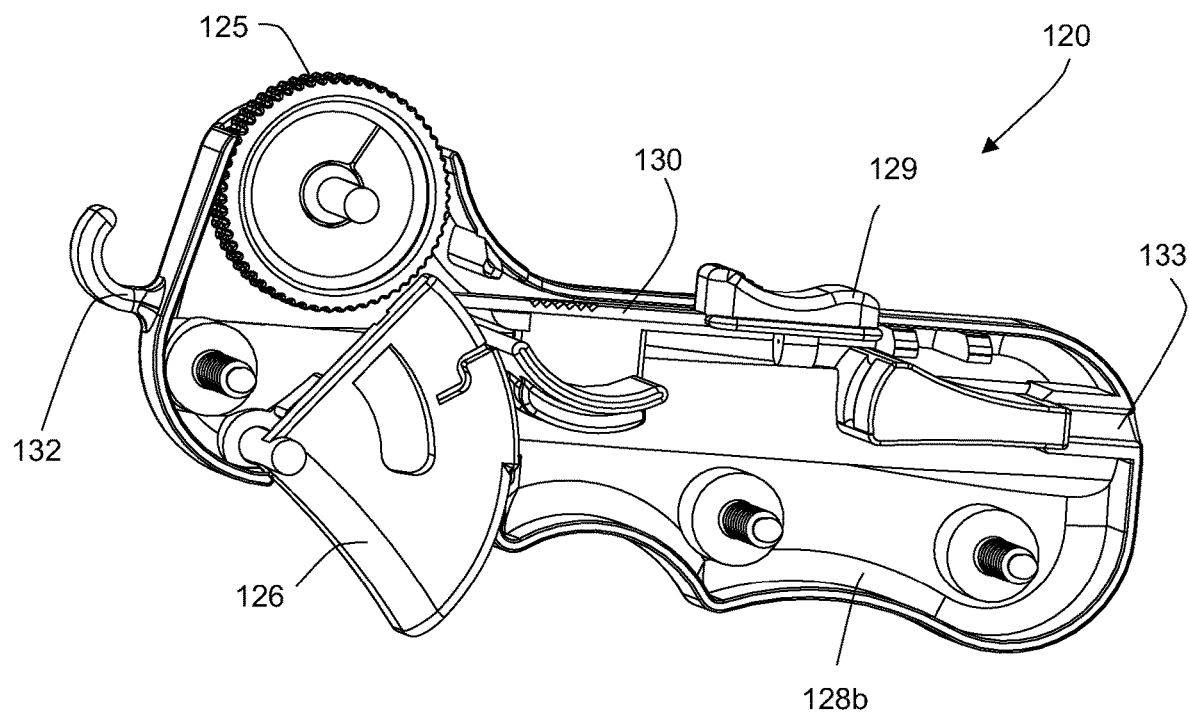
Figure 17:
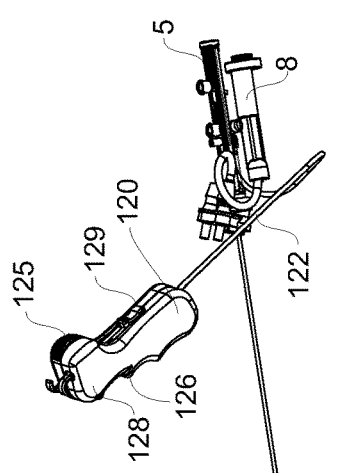
Figure 18:
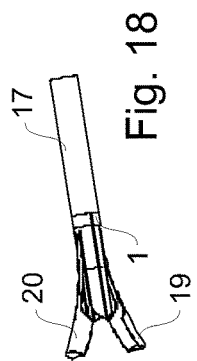
Figure 19:
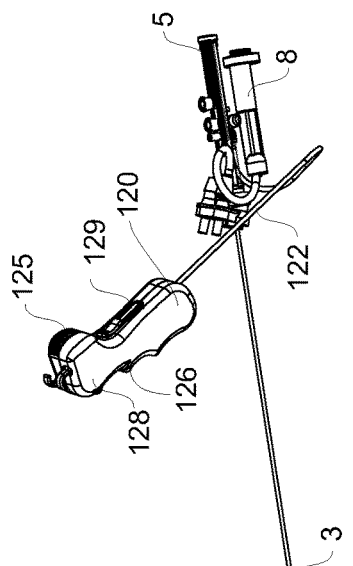
Figure 20:
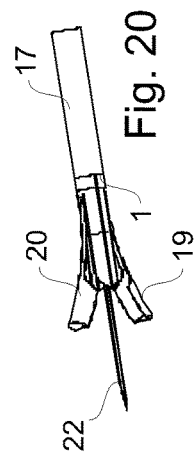

FIG. 1 is a perspective overview of an endosurgical device of the present invention in its operative set up environment ready for use in a biopsy procedure using a cystoscope, FIG. 2 is an enlarged cross-sectional view taken along line II-II in FIG. 1 of the tube, FIG. 3 is fragmentary perspective end view of an end effector, FIG. 4 a perspective, enlarged scale view of the endosurgical device seen in FIG. 1 mounted at a proximal handle part of a cystoscope, but with the electrical cord to the diathermy generator left out and liquid supply and discharge tubes left out, FIG. 5 shows, in perspective and in partial exploded view, the slide rail assembly, the tissue specimen collector and the adaptor, FIG. 6 shows the same in assembled state, FIG. 7 is an enlarged scale view of the adaptor of the device operating part seen from the side, FIG. 8 shows the flushing component from the holder end and the first operating end part, FIG. 9 shows the same from the second operating end part, FIGS. 10 and 11 are exploded, enlarged scale views of the endosurgical device seen from the distal guide end and the proximal guide end, respectively, of the main slide guide body without the spring members, the adaptor and the flushing component, FIG. 12 is a perspective, enlarged scale fragmentary view of the encircled fragment to the right in FIGS. 15 and 16 of the endosurgical device from the distal tube end and with remote actuator assembly, FIG. 13 shows the remote operating handle in perspective from above, FIG. 14 shows the same with a casing-half left out, FIG. 15 shows the endosurgical device in its starting position, FIG. 16 shows the endosurgical device in its configuration where the operating end of the endosurgical device has been exposed from the endoscope's working channel, FIG. 17 shows the endosurgical device with the effector sleeve retracted from the end effector, FIG. 18 shows the encircled operating end of the endosurgical device seen in FIG. 17 in an enlarged scale view, FIG. 19 shows the endosurgical device with the needle exposed between the jaws of the end effector, and FIG. 20 shows the encircled operating end of the endosurgical device seen in FIG. 19 in an enlarged scale view.

In the following it is by way of example assumed that the endoscope is a cystoscope and the organ, wherefrom tissue specimens are to be resected, is the urinary bladder. The example is non-limiting and it should be understood that the endosurgical device of the present invention can be used with many other kinds of endoscopes, and that the target tissue can be many different kinds of tissue. It is emphasized that scaling used in the figures are made to illustrate features of the invention the best possible way. Ratio of scaling up and down may differ between different figures. Scaling is chosen arbitrarily to illustrate components of the invention the best. Other end effectors, such as scissors and other forceps designs, can be used in the endosurgical device of the present invention.

FIG. 1 is a perspective overview of an endosurgical device 1 of the present invention in its operative set up environment ready for use in a biopsy procedure with an endoscope, e.g. in form of a cystoscope 2. A plurality of conventional diathermy generators, liquid sources, and reservoirs can be used in the biopsy procedure. Those are not shown in FIG. 1. Furthermore, for the purposes of visual overview the distal insertion tube of the cystoscope and the fiber optic have been left out. The multi-channel tube 3 is shown uncovered by the distal insertion part of the endoscope.

The endosurgical device 1 has a device operating part 4, which comprises plural sub-components: including at least a slide rail assembly 5, a remote actuator assembly 6, a flushing component 7, and a tissue specimen collector 8. Each of these sub-components 5,6,7,8 will be described separately and in combination in further details in the following figures, as well at their operative relationship will be explained and discussed.

The flexible multi-channel tube 3, in the following just referred to as the tube, used in the endosurgical device 1 seen in FIG. 1, is shown in enlarged cross-sectional view in FIG. 2.

The tube 3 has four lengthwise extending channels: a first lengthwise extending channel 9 for supplying liquid to the distal tube end 13 of the tube 3, a second lengthwise extending channel 10 for removing, e.g. by expelling or aspirating, liquid and other matter from the tube 3, such as tissue specimens, out via the proximal tube end 14, a third lengthwise extending channel 15 for a diathermy wire 76, and a fourth lengthwise extending channel 16 for reciprocating a needle. It could be said that the lengthwise extending channels "divide" the working channel of the endoscope into several sub-channels that improve the functionality of the endoscope to a hitherto unknown extent and dispense with the need to insert and retract different instruments through the working channel of the endoscope numerous times, thus saves time for biopsying, and confers comfort to the patient.

An embodiment of an end effector 21 is seen in FIG. 3 in an enlarged scale view. The effector sleeve 17 seen in FIG. 3 has an internal diameter selected for the end effector 21 to move tightly in and out of said effector sleeve 17, e.g. in response to reciprocating the end effector 17 at the distal tube end 14 of the tube 3 in and out of the effector sleeve 17, or by reciprocating the effector sleeve 17 over and away from the end effector 21, thus reciprocating the end effector and the effector sleeve in relation to each other once the effector-sleeve surrounded end effector 21 is placed in its biopsy position in front of the target site. When the end effector is in this biopsy position at the target site the jaws 19,20 are opened by retracting the effector sleeve, an optionally the endosurgical device is move further in contact with the target tissue. Next the tissue specimen is grasped by closing the jaws 19,20 by displacing the effector sleeve in the opposite direction above the end effector. The effector sleeve 17 may be a metal pipe or polymeric and the tube 3 may have an exterior structural reinforcement, such as a coil member, to provide the tube 3 with sufficient structure to be inserted into the working channel of the endoscope, and optionally to allow lengthwise movement in relation to the effector sleeve 17. In FIG. 3 of the end effector 17, the needle 22 has been exposed from the third lengthwise extending channel 16. The exterior structural reinforcement may be secured end-to-end to the effector sleeve and reciprocate simultaneously.

The end effector can be made from two pipe pieces each been given a tapered or blunt nose. The pipe pieces can be cut from separate pipes, e.g. by laser cutting lengthwise and providing the flexible members 19a,20a, hinge member 19a,20a. The pipe pieces are subsequently joined e.g. to obtain a main tubular body with spring-biased hinged jaws 19,20 thereby obtaining the end effector 21. The respective hinge members 19a,20a can deflect by itself to curve away when the effector sleeve is not covering the end effector, thus the end effector opens and closes resiliently.

FIG. 4 is an enlarged scale perspective view of the endosurgical device 1 seen in FIG. 1, but without the electrical wire that connects the endosurgical device 1 to the diathermy generator, and without the flushing and evacuation tubes 23,24 to a priming pump (not shown) and without liquid reservoirs and liquid sources. A priming pump may be associated with the diathermy generator and adapted to fill the tube system coupled to the tube 3, including flushing via the slide rail assembly 5 the first lengthwise extending channel 9 with non-conductive liquid and collect aspirated/discharged non-conductive liquid in connection with expelling tissue specimens from the second lengthwise extending channel 10.

The flushing component 7 has a first operating end part 18 adapted to be mounted to an endoscope fluid valve port by means of a first push-activated valve 25 and to an endoscope suction valve port of the cystoscope 2 using a second push-activated valve 26 to make the flushing component be operatively connected to said endoscope valve ports. An opposite second operating end part 27 of the flushing component 7 is in fluid communication with the slide rail assembly 5 and with the instrument port of the cystoscope 2 by means of an adaptor 28 at said second operating end part 27.

The second push-activated valve 26 opens and closes for the supply of liquid from a source of liquid (not shown), e.g. a drip bag, coupled to an infusion connection piece 38 to infuse liquid through the cystoscope via the infusion tube 31 of the flushing component 7. Similarly the first push-activated valve 25 opens and closes for suction through the endoscope via the suction tube 32, which suction tube 32 is coupled to a vacuum source via a suction connection piece 39.

The grip 29 makes it easy for the surgeon to hold on to the endosurgical device and the cystoscope at the same time by simply placing the hand on the cystoscope through the grip 29. The grip 29 may incorporate internal irrigation tubes or have external irrigation tubes 31,32 for flushing liquid, such as saline, and evacuating liquid again, respectively, from the hollow organ, such as the urinary bladder or other tissue surface, e.g. through the working channel of the cystoscope 2 via the tube 3, or through a liquid channel (not shown) of the cystoscope 2 especially allocated to said purpose prior to conducting biopsy. The non-conductive liquid used during diathermy to avoid accidental burning can be injected and sucked out in a similar manner.

The perspective, exploded view of FIG. 5 and the assembled view of FIG. 6 show the slide rail assembly 5, the tissue specimen collector 8 and the adaptor 28. Said adaptor 28 has a tubular adaptor body 33 that has a first adaptor end part 34 with a first adaptor end 35, which first adaptor end part 34 has a membrane (not shown) for inserting the tube 3, and an opposite second adaptor end part 36 with a second adaptor end 37 configured for coupling with the slide rail assembly 5.

The first adaptor end part 34 and the second adaptor end part 36 are, as seen best in the side view of FIG. 7, at an angle α in relation to each other, so that the slide rail assembly 5, which is secured to the second adaptor end part 36 is turned away from the cystoscope 2. The angle α is e.g. at least 45° to define a bend or curved flow channel through the tubular adaptor body 33.

The irrigation tubes 31,32 associated with the grip 29 are the infusion tube 31 and the suction tube 32. The suction tube 32 takes part in application of suction to empty the urinary bladder, and the infusion tube 31 takes part in infusing liquid to e.g. rinse the urinary bladder prior to the biopsy procedure and instill non-conductive liquid into the urinary bladder.

The adaptor 28 has a protruding flange 40 with seats 41,42. The seats 41,42 are adapted for mounting of a first coupling piece 43 and a second coupling piece 44 for providing fluid communication to the suction tube 32 and the infusion tube 31, respectively, and thus to the vacuum source (not shown) and the liquid source (not shown), respectively. The first and second coupling pieces 43,44 may e.g. be barbed bayonet male connectors, having respective barbed tapering first coupling ends 43a,44a and opposite second coupling ends 43b,44b with an enlarged diameter flange 43c,44c in-between said coupling ends 43a,44a;43b, 44b to promote the coupling pieces 43,44 staying in their respective seats 41,42 at the protruding flange 40.

As seen best in the enlarged scale detailed views of FIGS. 8 and 9 the flushing component 7 has a longitudinal grip 29 that extends between the first operating end part 18 and the second operating end part 27 of said flushing component 7. At the second operating end part 27 the flushing component 7 has a holder 30 for the slide rail assembly 5. The slide rail assembly 5 that is coupled to the tissue specimen collector 8 is docked in the holder 30 to be kept in a position protruding from the cystoscope 2. Both the slide rail assembly 5 and the tissue specimen collector 8 are thus located close to the proximal end of the cystoscope 2, and in convenient reach and view of the surgeon.

In use of the endosurgical device 1 the adaptor 28 is secured in the instrument port, the second operating end part 27 of the flushing component 7 is secured to the adaptor 28, the slide rail assembly 5, which is connected to the tissue specimen collector assembly 8, is mounted in the holder 30, and the tube 3 with needle 22, end effector 21, effector sleeve 17, and diathermy wire 76 is inserted through the membrane of the adaptor 28. The suction tube 32 is connected to the barbed tapering first coupling end 43a of the first coupling piece 43. The infusion tube 31 is connected to the second coupling end 44b of the second coupling piece 44. An intermediate tube 45 connects the tissue specimen collector 8 to the barbed coupling end 43a of the first coupling piece 43 to establish liquid communication to the suction tube 32 of the grip 29 to evacuate liquid from the tissue specimen collector 8.

The flushing tube 24 is connected to the tube coupling end 44a of the second coupling piece 44 to establish liquid communication to a primping pump (not shown). The opposite tube coupling end 44b of the second coupling piece 44 connects to a source of non-conductive liquid via the infusion tube 31 of the grip 29 thereby establishing liquid communication between priming pump (not shown) and source of non-conductive liquid (not shown). Non-conductive liquid can thus be consecutively replenished from same or another source coupled to the infusion tube 32 via the flushing component 7 after the closed biopsy cup has been evacuated by application of suction to the tissue specimen collector 8.

The slide rail assembly 5 has, as shown in FIGS. 5 and 6, a main slide guide body 46 for slidingly suspending an end effector slider 47, a junction slider 48, and a needle slider 49. The main slide guide body 46 is comprised of a tubular guide housing 50 with interior, opposite, lengthwise extending interior tracks 51. The opposite interior tracks 51 allow the end effector slider 47, the junction slider 48, and the needle slider 49 to reciprocate more or less to and from a proximal guide end 52 and an opposite distal guide end 53 of said main slide guide body 46. The main slide guide body 46 with the interior tracks 51 then defines a guideway 54 for the sliders 47,48,49 to reciprocate along.

A first spring member 55 is inserted in the tubular guide housing 50 between the end effector slider 47 and the junction slider 48, and a second spring member 56 is inserted between the junction slider 48 and the needle slider 49 to spring-bias any of said sliders 47,48,49 when they slide along the length of the guideway 54. In addition to the interior tracks 51 the wall 57 of the main slide guide body 46 also has a lengthwise extending opening 85, which is shorter than the interior tracks 51 to define the maximum possible stroke distance of the junction slider 48 and of the needle slider 49 in view of also the length of the end effector slider 47, but still allowing the end effector slider 47 to slide close to the distal guide end 53 of the main slide guide body 46.

The end effector slider 47 is connected to the effector sleeve, via a reinforcing coil 77, and by moving the reinforcing coil 77 in relation to the tube 3 by operating the end effector slider 47 the effector sleeve 17 moves lengthwise in relation to the end effector 17 and the jaws 19,20 open and/or close.

The junction slider 48 is connected to the proximal end 14 of the tube 3 and is in fluid communication with the first lengthwise extending channel 9 and the second lengthwise extending channel 10 of the tube 3. The junction slider 48 also provides electrical communication between the end effector 21 and a diathermy generator (not shown) by means of an electrical wire 76 through the third lengthwise extending channel 15 of the tube 3. The electrical wire 76 is kept insulated from liquid flowing inside the first and second lengthwise extending channels 9,10 by the surrounding tube's 3 wall. The electrical wire 76 is externalized via the junction slider 48 to be brought in electrical contact with the diathermy generator (not shown) to apply current to the end effector 21 to perform diathermy.

The structure of the end effector slider 47, the junction slider 48, and the needle slider 49 will be described in further details below.

The tissue specimen collector 8, which is seen in partly exploded assembled view in FIG. 5 and in assembled view in FIG. 6, has a main collector housing 58, a collector rack 59 with a series of adjacent chambers 60 for accommodating tissue specimens, and means 61 for moving the collector rack 59 lengthwise along the longitudinal axis of the main collector housing 58, which means 61 in the present exemplary embodiment is a screw rod 62 that engages with a threaded hole 63 or bore in the collector rack 59. The screw rod 62 has a rotating knob 64 at a free end 65 facing away from the collector rack 59 and an opposite end 66 that threadingly engages the collector rack 59 to displace said collector rack 59 in response to rotating the rotating knob 64.

The main collector housing 58 is tubular and has a proximal housing end 67 that is threaded to mount a detachable cap 69, and an axially opposite liquid outlet 68 to be coupled to the intermediate tube 45, as seen in e.g. FIG. 4, to discharge flushing liquid entering the tissue specimen collector 8 from the junction slider 48 of the slide rail assembly 5 when the second lengthwise extending channel 10 is being flushed or evacuated to carry a tissue specimen out of the tube 3.

Other kinds of coupling means between the main collector housing 58 and the detachable cap 69, such as male and female snap couplings are also suitable within the scope of the present invention. The detachable cap 69 facilitates that the collector rack 59 with the tissue specimens can be taken out of the main collector housing 58 after completing the biopsy procedure. The free end 65 of the screw rod 62 passes through a cap hole 70 in the detachable cap 69 so that the rotating knob 64 is accessible from outside the main collector housing 58. Preferably, the cap hole 70 is at the centre of the detachable cap 69 to allow the screw rod 62 to rotate, which cap hole 70 thus also serves to keep the screw rod 62 substantially centered during the surgery so that the position of the chambers 70 is easily shifted and the collector rack 59 does not skew or gets misaligned during its translatory movement in the main collector housing 58.

The main collector housing 58 has a collector port 71a coupled to a protruding coupling piece 71 for fluidly coupling to a sample port 72 of the junction slider 48, which sample port 72 protrudes from the lengthwise extending opening 85 of the tubular guide housing 50 of the main slide guide body 46.

The main collector housing 58 has at least two lengthwise extending sections: a proximal tubular housing end part 74 and a distal tubular housing end part 75 in extension thereof. The proximal tubular housing end part 74 accommodates the screw rod 62, and depending on which chamber 60 of the series of chambers of the collector rack 59 that is brought into communication with the sample port 72 via the coupling piece 71, the proximal tubular housing end part 74 also accommodates more or less of the length of said collector rack 59. The proximal tubular housing end part 74 ends in the proximal housing end 67. Opposite said proximal housing end 67 the proximal tubular housing end part 74 extends into the distal tubular housing end part 75 that, depending on which chamber 60 of the series of chambers of the collector rack 59 that is brought into communication with the sample port 72 via the coupling piece 71, accommodates the entire collector rack 59 or a part of the collector rack 59 only. The cross-section of the distal tubular housing end part 75 may corresponds substantially to the cross-section of the collector rack 59, to avoid that the collector rack 59 rotates inside the distal tubular housing end part 75 about its longitudinal axis so that a chamber 60 cannot be aligned with the sample port 72 of the junction slider 48.

The sliders 47,48,49 are shown in perspective in FIGS. 10 and 11, and assembled into the slide rail assembly 5 in FIG. 12. FIGS. 10 and 11 also show, in perspective, the tube 3 and the reinforcing coil member 77 for the tube 3, which reinforcing coil member 77 may be secured distally to the effector sleeve 17 by an end-to-end joint, e.g. by means of an exterior heat-shrinking tube. FIGS. 10 and 11 further show the needle 22, the diathermy wire 76, and the sheave assembly 78 from different ends. The spring members 55,56 are left out to better overview the structural features of the sliders 47,48,49 and of the main slide guide body 46.

The end effector slider 47 has a first bifurcated main body 79 with a tubular front connection piece 80 that allows the tube 3 to pass through its lumen to reach the junction slider 48 where it is mounted so that the junction slider can slide all of the tube 3, the reinforcing coil member 77, the effector sleeve 21, and the end effector 21 in combination and simultaneously.

The reinforcing coil member 77 is connected to a tubular front connection piece 80 of the end effector slider 47 and oppositely to the effector sleeve 21 to reciprocate the effector sleeve 21 to open and close the jaws 19,20.

The first spring member 55 can be positioned between opposite first legs 81,82 of the first bifurcated main body 79 to aid in spring-biasing any of the sliders 47,48,49. The junction slider 48 can move in the lengthwise extending opening 85 of the tubular guide housing 50 of the main slide guide body 46 towards the distal guide end 53 of said main slide guide body 46 between the first legs 81,82 of the end effector slider 47 until it hits on the end stop 83 constituted by the distal end 84 of the lengthwise extending opening 85 of the main slide guide body 46. The exterior wall 86 of the end effector slider 47 has opposite lengthwise extending protrusions 87 that slide in the interior tracks 51 of the tubular guide housing 50 of the main slide guide body 46. A first operating string securing arm 88 protrudes from the end effector slider 47 close to the tubular front connection piece 80 in a plane below the first bifurcated main body 79. The first operating string securing arm 88 has a first eye or hole 89 for securing of or passage of a first operating string 116 connected to a trigger button 125 of the remote operating handle 120 of the remote actuator assembly 6, as will be explained in further details with references to FIGS. 11-14.

The junction slider 47 has a slide part 90 and protruding first sliding shoes 91 of dimensions selected to control and facilitate smooth sliding of the junction slider 48 along the interior tracks 51 and along the guideway 54. The junction slider 47 can also slide between the first legs 81,82 of the end effector slider 47. The junction slider 48 further has a main junction body 92 with a through-going axially extending bore 93 that receives the tube 3, whereby the first lengthwise extending channel 9 is put in fluid communication with an inlet port 94 of the junction slider 48, and the second lengthwise extending channel 10 is put in liquid communication with the sample port 72 of the junction slider 48. The slide part 90 may be a front part of the main junction body 92. The opposite first sliding shoes 91 protrude from the main junction body 92 to slide in the interior tracks 51. A bearing 119 for a sheave member 73 of a sheave assembly 78 protrudes from the main junction body 92 through the lengthwise extending opening 85 of the main slide guide body 46. The bearing 119 has a coupling hole 121 for attaching a sheave assembly 78 of the remote actuator assembly 6, e.g. attaching a shaft or pin. The sheave member may be rotationally arranged in the bearing 119 or be stationary.

The electrical diathermy wire 76 runs inside the third lengthwise extending channel 15 and is externalized via a diathermy port 95 of the junction slider 47, which diathermy port 95 is further configured for plugging in an electrical plug (not shown) of the diathermy generator (not shown).

The through-going bore 93 extends lengthwise through the main junction body 92 inside the fourth lengthwise extending channel 16 of the tube 3 to allow the needle 22 to pass through to reach the needle slider 49. The fourth lengthwise extending channel 16 of the tube 3 is radially offset the longitudinal axis of the tube, optionally all lengthwise extending channels are radially offset the longitudinal axis of the tube.

A second operating string securing arm 96 protrudes from the junction slider 48 in a plane below the main junction body 92. The second operating string securing arm 96 has a second eye of hole 97 for guiding the operating strings of the remote actuator assembly 6, which is seen in FIG. 12.

The needle slider 49 is also bifurcated in that it has a second bifurcated main body 98 constituted by opposite second legs 99,100 that join in an injection port 101 in liquid communication with the needle 22. The second legs 99,100 is configured to grasp around the sample port 72 of the junction slider 48 to allow the sample port 72 to slide in-between said second legs 99,100.

In order to couple to the junction slider 48 and the needle slider 49, the tube 3 may be divided in respective sub-tubes with the first lengthwise extending channel 9 turned in communication with the inlet port 94 of the junction slider 48, the second lengthwise extending channel 10 turned in communication with the sample port 72 of the junction slider 48, the third lengthwise extending channel 15 turned in communication with the diathermy port 95 of the junction slider 48, and the fourth lengthwise extending channel 16 directed into or towards the injection port 101 of the needle slider 49 via the junction slider 48. The fourth lengthwise extending channel 16 of the tube 3 may seal around the needle 22 that runs inside the fourth lengthwise extending channel 16 of the tube 3. The needle 22 alone, or the fourth lengthwise extending channel 16 and the needle 12, may continue into the injection port 101. Other arrangements of obtaining liquid communication between the injection port 101 and the needle 22 are within the scope of the present invention. Medicament may be injected into the needle 22 via the injection port 101, e.g. by using a hypodermic needle to penetrate a membrane (not shown) of the injection port.

The needle slider 49 has a protruding curved flexible clamp 102 that conforms around the exterior wall of the tubular guide housing 50 of the main slide guide body 46. Thus the needle slider 49 may be slidingly snapped on the main slide guide body 46. The protruding curved flexible clamp 102 also has a third eye of hole 104 below the second bifurcated main body 98 to also serve as a securing arm 103 for a third operating string 118 to put the needle slider 49 in operative communication with the remote actuator assembly 6, thus to move the needle 22 in and out of the end effector 22.

A detachable cover or plug 105 can open and close the proximal guide end 52 of the main slide guide body 46 to mount the sliders 47,48,49 and the spring members 55,56 in the guideway 54. The detachable cover or plug 105 may have an indent or similar coupling component 106 to mate firmly with mating means 107 at a free holder end 108 of the holder 30. To that aspect the end 109 of the holder 30 opposite the free holder end 108 has a hole 110 for inserting the tube 3 and for guiding said tube 3 into the instrument port of the cystoscope 2 via the adaptor 28.

The tubular guide housing 50 has a fourth eye 111 at the proximal guide end 52 and a fifth eye 112 at the opposite distal guide end 53.

The sheave assembly 78 includes a sheave member 113 having a first sheave track 114 and a second sheave track 115, a first operating string 116, a second operating string 117, and a third operating string 118. The sheave member 113 is suspended in the bearing 119 of the junction slider 48 and extends through the lengthwise extending opening 85 of the tubular guide housing 50 of the main slide guide body 46 and below said tubular guide housing 50 to keep the second operating string 117 under control and free of entangling with the first operating string 116 and the third operating string 118.

The second operating string 117 has a second distal string end 117a secured to the fifth eye 112 at the distal guide end 53 of the tubular guide housing 50 of the main slide guide body 46. The second operating string 117 then runs around the first track 114 of the sheave member 113 of the sheave assembly 78 through the second eye 97 of the junction slider 48 further inside the guide tube 122, such as a Bowden conduit, and is fixed to the wheel button 125, such as a thumb wheel or roller, of the remote operating handle 120. From its fixation point at the wheel button 125 the second operating string 117 returns again inside the guide tube 122 via a second track 115 of the sheave member 113 of the sheave assembly 78 to have its second proximal string end 117b secured to a fourth eye 111 at the proximal guide end 52 of the tubular guide housing 50 of the main slide guide body 46. The second operating string 117 can then reciprocate the junction slider 48 to move the operating end 131 of the endosurgical device 1 of the present invention, thus the distal tube end 13 with the end effector 21 surrounded by the effector sleeve 17, in and out of the distal opening of the working channel of the cystoscope to position said operating end towards the target site.

This arrangement of the second operating string 117 minimizes slack and play, and the required dimension of guide tube 122, which e.g. is a Bowden conduit, is much smaller than if it would have been used in compression, thereby avoiding buckling of the guide tube 122 and trapping of the operating strings 116,117,118 extending therein.

The remote operating handle 120 of the remote actuator assembly 8 is seen in perspective oblique from the side, and in the interior view of FIG. 14 of the same a casing half 128a of the opposite casing halves 128a,128b of a casing 128 of the remote operating handle 120 has been left out to visualize the arrangement of the trigger button 126, the wheel button 125 and the slider button 129 and the operating strings 116,117,118. The casing 128 has a snap-on means 132 at it foremost end to snap the remote operating handle 120 to the distal tube part (not shown) of the cystoscope 2. Opposite the snap-on means 132 the casing has en entry for the tube guide 122. The snap-on means 132 is suited to detachable snap the remote operating handle 120 on to the distal tube part of the cystoscope 2 perpendicularly protruding therefrom. Further or other snap-on means can be provided otherwise on the casing to facilitate other snap-on orientations of the remote operating handle 120.

The wheel button 125 may have its rotating shaft spring-suspended. In its normal position the wheel button 125 is locked against the casing 128 of the remote operating handle 120 by the wheel button 125 engaging the casing 128. When pushing the wheel button 125 down again in its operating opening 127 the axis of the rotating shaft shifts and the wheel button 125 releases from its engagement with the casing 128 and can rotate again. The locking arrangement of the wheel button 125 in relation to the casing 128, inside and free of its operating opening 127, is seen in enlarged scale view in FIG. 14. The remote operating handle is seen in assembled state in FIG. 13.

None of the spring members 55,56 are involved to expose the operating end 131 of the endosurgical device 1 of the present invention from the working channel of the cystoscope 2.

A first operating string 116 has a first distal string end 116b secured to the trigger button 126 at the remote operating handle 120. The first operating string 116 extends via the guide tube 122 towards its proximal string securing end 116a to be attached to the end effector slider 47, e.g. to the first eye 89. Moving the end effector slider 47 backwards by actuating the trigger button 126 pulls the effector sleeve 21 free of the end effector 17, and compresses the first spring member 55 against the junction slider 48, thereby allowing the jaws 19,20 of the end effector 21 to spring apart. When releasing the trigger button 126, the spring force of the first spring member 55 closes the jaws 19,20 of the end effector 21 with a limited force to avoid damage to the end effector 21 thereby ensuring repeatable conditions for the electrosurgical resecting sequence.

A third operating string 118 has a third proximal string end 118a secured to the third eye 104 of the needle slider 49, and an opposite third distal string end 118b secured to a slider button 129 of the remote operating handle 120 to reciprocate the needle slider 49 between the opposite jaws 19,20. When the slider button 129 is moved forward towards the junction slider 48 the second spring member 56 is compressed which places a spring force on the needle slider that makes the needle 22 to retract by retracting the needle slider 49 once the slider button releases the compression force on the second spring member 56.

To keep control of when the actions of the slider button 129, and thus release of the compression force of the second spring member 55, the slider button 129 may have a ratchet extension 130 facing the trigger button 126. The ratchet extension 130 can engage a mating ratchet on the trigger button 126 to interlock the slider button 129 and the trigger button 126 so that the trigger button 126 does not unintentionally releases the spring force of the first spring member 55 and unintentionally pushes the effector sleeve 17 forward to close the jaws 19,20 while the needle is still exposed between said jaws 19,20.

FIG. 15 shows the endosurgical device in its starting position. None of the spring members 55,56 are biased, the end effector 21 is inside the effector sleeve 17, and the wheel button 125 is locked to the casing 128 in its operating opening 127.

In the situation seen in FIG. 16 the wheel button 125 has been unlocked and rotated to advance the operating end of the endosurgical device 1 from the distal end of the cystoscope (not shown). During this advancing the junction slider 48 moves forward due to the second operating string's 117 coupling to the sheave member 73 of the junction slider 48. The needle 22, which is connected to the needle slider 49 slides inside or along the junction slider 48 when the junction slider moves in the guideway 54.

In the situation seen in FIG. 17 the trigger button 126 has been actuated to expose the end effector 21 from the effector sleeve 17 whereby the opposite jaws 19,20 of the end effector 21 open. When depressing the trigger button 126 the first operating string 116 is pulled at, and the first operating string 116 pulls the end effector slider 47 towards the proximal guide end 52. The junction slider is thereby in a position at least partly between the opposite legs 81,82 of the end effector slider 47, which end effector slider 47 retracts the reinforcing coil to which the effector sleeve is mounted end-to-end, thereby leaving the end effector 21 free and allowing the opposite jaws 19,20 to inherently open, as seen in the enlarged scale view of FIG. 18 of the operating end 131 of the endosurgical device 1.

Due to the securing of the third operating string 118 to both the slider button 129 and the needle slider 49, the needle slider 49 can be moved towards the junction slider 48 by sliding the slider button 129 forward, and thereby moving the needle 22 out between and beyond the open jaws 19,20, as seen in FIGS. 19 and 20 to make an injection. To make sure that the jaws do not close unintentionally while the needle 22 is exposed the slider button 129 and the trigger button 126 engage during the injection.

The needle is retracted by moving the slider button in the opposite direction, the jaws are then closed around the tissue by releasing the trigger button to move the effector sleeve forward. And diathermy is applied, e.g. by operating a foot pedal of the diathermy generator to resect the tissue specimen.

Regarding the end effector 21, said end effector has opposite jaws 19,20 arranged to diverge from a longitudinal axis of the end effector in a relaxed condition when the end effector 21 is at least partly outside the effector sleeve 17, due to flexible members 19a,20a.

An exterior plastic tubing may be heat-shrinked around the length of the of the endosurgical device to seal joints and insulate the endosurgical device from the working channel, and combining the coiled reinforcing member end-to-end to the effector sleeve, e.g. by heat fusion, to enable the effector sleeve to move lengthwise to open and close the jaws by operating the end effector slider.

The multi-functional endosurgical device of the present invention suggests a whole new way to take biopsies from a hollow organ. Completely new conditions are created for the treatment of these patients. The costs can be drastically reduced and the patient benefit is extremely high. It will be possible to diagnose and correct outpatients with cancers in a few minutes on a regular visit. Patients no longer need any catheter treatment after surgery, which means they eliminate the high risk of urinary tract infection that a catheter entails. All different categories of staff no longer need to be involved; it is enough with a doctor and nurse, which means a huge cost reduction, and patients can receive cancer treatment much faster, and surgical capacity for other purposes are released.

The invention claimed is:

1. An endosurgical device comprising:
   a tube having a proximal tube end and an opposite distal tube end, and at least one lengthwise extending channel extending there-between,
   an end effector provided at the opposite distal tube end, and
   a device operating part at the proximal tube end, wherein the tube has a first lengthwise extending channel of the at least one lengthwise extending channel for supplying a liquid to the end effector, a second lengthwise extending channel of the at least one lengthwise extending channel for removing matter from or at the end effector, and a third lengthwise extending channel of the at least one lengthwise extending channel for accommodating an electrical wire connected to the end effector to apply current to perform diathermy, an effector sleeve surrounds the tube at least at the opposite distal tube end of said tube, and being arranged to enclose at least at the opposite distal tube end of the tube, the device operating part comprises a slide rail assembly, the slide rail assembly comprises at least a main slide guide body that accommodates an end effector slider and a junction slider, the main slide guide body has a guideway with a proximal guide end and an opposite distal guide end that receives the tube, the end effector slider is adapted to slide in the guideway at the opposite distal guide end, and is connected to the effector sleeve to operate said effector sleeve in relation to the end effector, and the junction slider is adapted to slide in the guideway between the proximal guide end and the end effector slider, the junction slider is connected to the tube to arrange the first lengthwise extending channel of the at least one lengthwise extending channel, the second lengthwise extending channel of the at least one lengthwise extending channel and the third lengthwise extending channel of the at least one lengthwise extending channel of the tube in communication with the end effector.

2. The endosurgical device according to claim 1, wherein the slide rail assembly further has a needle slider disposed in the guideway in front of the junction slider at the proximal guide end, the needle slider has a needle or a nozzle secured thereto, the needle or nozzle is arranged inside a fourth lengthwise extending channel of the at least one lengthwise extending channel of the tube between a first needle position in which the needle or the nozzle is in a retracted position and a second needle position in which the needle or the nozzle is exposed from the end effector.

3. The endosurgical device according to claim 2, wherein the needle or the nozzle extends from the proximal tube end through the junction slider to be connected to the needle slider.

4. The endosurgical device according to claim 2, wherein the needle slider has an injection port for injecting a liquid into the needle or the nozzle.

5. The endosurgical device according to claim 1, wherein the junction slider has at least one of:
an inlet port in fluid communication with the first lengthwise extending channel of the at least one lengthwise extending channel for delivering a flushing liquid at and/or to the end effector,
a diathermy port in communication with the third lengthwise extending channel of the at least one lengthwise extending channel, and/or
a sample port in communication with the second lengthwise extending channel of the at least one lengthwise extending channel for coupling with a tissue specimen collector, and/or for removing matter from a biopsy site, and/or for transferring matter confined within the end effector or held by the end effector out of the endosurgical device.

6. The endosurgical device according to claim 1, wherein the slide rail assembly further has a first spring member inserted between the end effector slider and the junction slider and/or a second spring member inserted between the junction slider and a needle slider.

7. The endosurgical device according to claim 1, wherein the device operating part further comprises a remote actuator assembly for operating the slide rail assembly, the remote actuator assembly has a remote operating handle with buttons allocated to operate the end effector slider, the junction slider and a needle slider, and is operatively connected to the end effector slider, the junction slider, and the needle slider via respective operating strings.

8. The endosurgical device according to claim 7, wherein the remote actuator assembly comprises a sheave assembly, the sheave assembly is located at the junction slider to move together with said junction slider in response to pulling the operating strings by operating the respective buttons on the remote operating handle.

9. The endosurgical device according to claim 7, wherein the remote actuator assembly includes:
a first operating string having a first proximal string end secured to the end effector slider and an opposite first distal string end secured to a trigger button of the remote operating handle to operate the effector sleeve,
a second operating string having a second distal string end secured to a distal guide end of a tubular guide housing of the main slide guide body, the second operating string runs around a first track of a sheave assembly via a fixed point at a wheel button of the remote operating handle and returns from the wheel button to a proximal end of the tubular guide housing of the main slide guide body via a second track of the sheave assembly to have a second proximal string end secured to a proximal guide end of the tubular guide housing, and
a third operating string having a third proximal string end secured to the needle slider, and an opposite third distal string end secured to a slider button of the remote operating handle to move the needle slider and the needle.

10. The endosurgical device according to claim 1, wherein the device operating part further comprises a flushing component having a first operating end part adapted to be mounted to an endoscope fluid valve port and to an endoscope suction valve port of an endoscope, and an opposite second operating end part adapted to be set in fluid communication with the slide rail assembly and with an instrument port of the endoscope.

11. The endosurgical device according to claim 10, wherein the endosurgical device further comprises an adaptor having a tubular adaptor body that has a first adaptor end part with a first adaptor end, the first adaptor end part has a membrane for inserting the tube and is dimensioned to replace an end cap of the instrument port, and an opposite second adaptor end part with a second adaptor end configured for coupling with the slide rail assembly and the flushing component.

12. The endosurgical device according to claim 11, wherein the first adaptor end part and the opposite second adaptor end part are at an angle in relation to each other.

13. The endosurgical device according to claim 12, wherein the adaptor is rotatably arranged in the instrument port about a central axis of the instrument port.

14. The endosurgical device according to claim 13, wherein the adaptor is arranged to rotate at least 45° in the instrument port about a central axis of the instrument port.

15. The endosurgical device according to claim 12, wherein the slide rail assembly is rotatable arranged about a central axis of the endoscope's instrument port in relation to the adaptor.

16. The endosurgical device according to claim 11, wherein the adaptor is adapted for mounting of coupling pieces for mounting one or more tubes to one or more of a liquid reservoir, a drainage reservoir, an inlet port of the junction slider, a sample port of the junction slider, a collector port or coupling piece to a tissue specimen collector secured to the sample port of the junction slider or a liquid outlet from a tissue specimen collector that is secured to the sample port of the junction slider.

17. The endosurgical device according to claim 16, wherein the tissue specimen collector is a multi-chamber collector for directly collecting a resected tissue specimen as the resected tissue exits the sample port in the order the resected tissue is resected.

18. The endosurgical device according to claim 1, wherein the end effector has opposite jaws arranged to diverge from a longitudinal axis of the end effector in a relaxed condition when the end effector is at least partly outside the effector sleeve.

19. The endosurgical device according to claim 18, wherein the end effector has a flat nose.

* * * * *